United States Patent
Nuopponen et al.

(10) Patent No.: US 12,227,761 B2
(45) Date of Patent: Feb. 18, 2025

(54) SUPPORTIVE NANOFIBRILLAR CELLULOSE SCAFFOLD FOR EXPANDING CELLS

(71) Applicant: UPM-KYMMENE CORPORATION, Helsinki (FI)

(72) Inventors: Markus Nuopponen, Helsinki (FI); Lauri Paasonen, Järvenpää (FI); Susanna Narkilahti, Kangasala (FI); Tiina Joki, Lempäälä (FI); Laura Ylä-Outinen, Tampere (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 714 days.

(21) Appl. No.: 16/624,756

(22) PCT Filed: Jun. 19, 2018

(86) PCT No.: PCT/FI2018/050478
§ 371 (c)(1),
(2) Date: Dec. 19, 2019

(87) PCT Pub. No.: WO2018/234634
PCT Pub. Date: Dec. 27, 2018

(65) Prior Publication Data
US 2020/0115678 A1    Apr. 16, 2020

(30) Foreign Application Priority Data
Jun. 22, 2017  (EP) ..................................... 17177368

(51) Int. Cl.
*C12N 5/0793* (2010.01)
*C08B 15/02* (2006.01)

(52) U.S. Cl.
CPC ............ *C12N 5/0619* (2013.01); *C08B 15/02* (2013.01); *C12N 2501/73* (2013.01); *C12N 2502/081* (2013.01); *C12N 2513/00* (2013.01); *C12N 2533/78* (2013.01)

(58) Field of Classification Search
CPC .............. C12N 5/0619; C12N 2501/73; C12N 2502/081; C12N 2513/00; C12N 2533/78; C08B 15/02
See application file for complete search history.

(56) References Cited

U.S. PATENT DOCUMENTS

| | | | |
|---|---|---|---|
| 5,254,471 A | 10/1993 | Mori | |
| 7,449,180 B2 | 11/2008 | Kisiday | |
| 9,593,304 B2 * | 3/2017 | Laukkanen | ............ C12M 23/14 |

FOREIGN PATENT DOCUMENTS

| | | | | |
|---|---|---|---|---|
| EP | 1970436 B1 | 5/2012 | | |
| EP | 2782937 A1 | 10/2014 | | |
| EP | 2633032 B1 | 2/2015 | | |
| EP | 2633033 B1 | 4/2016 | | |
| JP | 2009-173909 A | 8/2009 | | |
| JP | 2010209510 A | 9/2010 | | |
| JP | 2015-530104 A | 10/2015 | | |
| JP | 2016-501926 A | 1/2016 | | |
| RU | 2665359 C2 | 8/2018 | | |
| WO | 2004007683 A2 | 1/2004 | | |
| WO | WO-2009084566 A1 * | 7/2009 | ............ | C08B 15/02 |
| WO | 2009126980 A1 | 10/2009 | | |
| WO | 2014049204 A1 | 4/2014 | | |
| WO | 2014068196 A2 | 5/2014 | | |
| WO | 2015011337 A1 | 1/2015 | | |
| WO | 2015015056 A1 | 2/2015 | | |

OTHER PUBLICATIONS

Joki, T., et al. "Plant Derived Nanofibrillar Cellulose (NFC) Hydrogel Supports Robust Human Neuronal Network Formation in vitro." (Year: 2017).*

Bhattacharya et al., (2012) Nanofibrillar cellulose hydrogel promotes three-dimensional liver cell culture. Journal of Controlled Release, 164(3) pp. 291-298 (Year: 2012).*

Notice for Reasons of Refusal in Japanese Patent Application No. JP570369/2019, mailed Mar. 2, 2021 (8 pages).

Viviana R. Lopes et al: "In vitro biological responses to nanofibrillated cellulose by human dermal, lung and immune cells: surface chemistry aspect", Particle and Fibre Toxicology, vol. 14, No. 1, Jan. 10, 2017 (14 pages).

International Search Report in International Patent Application No. PCT/FI2018/050478, mailed Oct. 19, 2018 (3 pages).

Ahola, S., Turon, X., Osterberg, M., Laine, J., Rojas, O.J. 2008. Enzymatic hydrolysis of native cellulose nanofibrils and other cellulose model films: effect of surface structure. Langmuir, 24, 11592-11599 (8 pages).

Hoffman, A.S., 2002. Hydrogels for biomedical applications. Advanced Drug Delivery Reviews, vol. 54, No. 1, pp. 3-12 (10 pages).

Geckil, H., Xu, F., Zhang, X., Moon, S. and Demirci, U. 2010. Engineering hydrogels as extracellular matrix mimics. Nanomedicine (Lond),. 5(3): p. 469-84 (16 pages).

Koivisto, J.T., Joki, T., Parraga, J., Pääkkönen, R., Ylä-Outinen, L., Salonen, L., Jonkkari, I., et al. 2017. Bioamine-Crosslinked Gellan Gum Hydrogel for Neural Tissue Engineering. Biomedical Materials, February, 1-38. doi:10.1088/1748-605X/aa62b0 (16 pages).

Kutcharlapati et al., 2008. Metals Materials and Processes 20(3):307-314 (9 pages).

Lappalainen, R.S., et al.; "Similarly Derived and Cultured hESC Lines Show Variation in Their Developmental Potential towards Neuronal Cells in Long-Term Culture"; Regenerative Medicine 5 (5): 749-62. doi:10.2217/rme.10.58; 2010 (14 pages).

Nisbet DR, et al.; "Neural tissue engineering of the CNS using hydrogels"; J Biomed Mater Res B Appl Biomater 87: 251-263; 2008 (13 pages).

(Continued)

*Primary Examiner* — Kara D Johnson
(74) *Attorney, Agent, or Firm* — NIXON PEABODY LLP

(57) ABSTRACT

The present invention is related to methods and materials for culturing expanding cells in a three-dimensional culture. The material comprises plant-derived anionic nanofibrillar cellulose, wherein the anionic nanofibrillar cellulose is in a form of hydrogel. The invention also provides methods for producing materials and compositions comprising plant-derived anionic nanofibrillar cellulose.

16 Claims, 19 Drawing Sheets

(56) References Cited

OTHER PUBLICATIONS

Ylä-Outinen, L., et al.; "Three-Dimensional Growth Matrix for Human Embryonic Stem Cell-Derived Neuronal Cells"; Journal of Tissue Engineering and Regenerative Medicine 8 (3): 186-94. doi:10.1002/term.1512; 2014 (p ages).
Nechyporchuk, O., et al.; "Production of cellulose nanofibrils: A review of recent advances"; Industrial Crops and Products 93 (2016) 2-25; 2016 (24 pages).
European Search Report for Application No. EP 17177368, dated Oct. 13, 2017 (2 pages).
M.A. Sadovoy et al.: "Cellular Matrices (Scaffolds) for Bone Regeneration: State of the Art", Hir. Pozvonoc. 2014; (2):79-86 (8 pages).
Federal Service for Intellectual Property Patent Search Report in Russian Patent Application No. 2019142313, dated Sep. 2, 2021(4 pages w/English translation).
Office Action in Russian Patent Application No. 2019142313, mailed on Oct. 15, 2021 (7 pages).
Hua, K. et al., "Translational study between structure and biological response of nanocellulose from wood and reen algae," RSC Adv. 4, pp. 2892-2903 (2014).
GrowDex Hydrogel Range; https://www.upmbiomedicals.com/siteassets/documents/growdex-hydrogels-product-brochure-2021.pdf; (8 pages).
Yan-Ru Lou, et al; "The Use of Nanofibrillar Cellulose Hydrogel as a Flexible Three-Dimensional Model to Culture Human Pluripotent Stem Cells" Stem Cells and Development; vol. 23, No. 4; No. 4, 2014; https://www.liebertpub.com/doi/full/10.1089/scd.2013.0314; (13 pages).

\* cited by examiner

1A

1B

1C

SUPPORTIVE NANOFIBRILLAR CELLULOSE SCAFFOLD FOR EXPANDING CELLS

CROSS-REFERENCE TO RELATED APPLICATIONS

This application is a U.S. National Stage of International Application No. PCT/FI2018/050478 filed Jun. 19, 2018, which claims the benefit of European Application No. 17177368.2 filed Jun. 22, 2017, both of which are hereby incorporated by reference in their entireties.

FIELD OF THE INVENTION

The present invention relates to the field of cell culture systems and cell technology. The invention relates to plant-derived cell culture compositions comprising anionic nanofibrillar cellulose.

BACKGROUND

A neuron is a specialized type of cell found in the bodies of all eumetozoans (i.e. from all major animal groups except sponges, placozoa, and several other extinct or obscure life forms). Thus, only sponges and a few other simpler animals lack neurons. The features that define a neuron are electrical excitability and the presence of synapses, which are complex membrane junctions that transmit signals to other cells. The body's neurons, plus the glial cells that give them structural and metabolic support, together constitute the nervous system. In vertebrates, the majority of neurons belong to the central nervous system (CNS), but some reside in peripheral ganglia, and many sensory neurons are situated in sensory organs such as the retina and cochlea.

A typical neuron is divided into three parts: the soma or cell body, dendrites, and axon. The soma is usually compact; the axon and dendrites are filaments that extrude from it. Dendrites typically branch profusely, getting thinner with each branching, and extending their farthest branches a few hundred micrometers from the soma. Synaptic signals from other neurons are received by the soma and dendrites; signals to other neurons are transmitted by the axon. Neurons communicate by chemical and electrical synapses in a process known as neurotransmission, also called synaptic transmission.

In most cases, neurons are generated by special types of stem cells. Neurons in the adult brain generally do not undergo cell division. Thus, neurogenesis largely ceases during adulthood in most areas of the brain. Astrocytes are star-shaped glial cells that have also been observed to turn into neurons by virtue of the stem cell characteristic pluripotency.

Neuronal tissue engineering is a promising new therapeutic method and many biomaterials have been tested for neuronal applications. In tissue engineering, biomaterials are designed to improve the function of the tissue or organ in the human body. Neuronal tissue engineering is an area in which combining cells, biomaterials, and growth factors is aimed at assembling a product that can be transplanted into patients suffering neurotrauma or diseases of the central or peripheral nervous system. In neuronal tissue engineering, biomaterials can support cell growth, support tissue structure, or improve the tissue/cell function. Biomaterials for neural tissue engineering should be non-toxic, 3D, support the growth of the desired cell type, and allow for nutrition flow.

Extracellular matrix-based materials (ECM), such as collagen, laminin, and fibronectin, are most commonly used for neural guidance structures. In addition, hyaluronic acid- and alginate-based materials are widely used natural material groups for peripheral nerve guidance. Even more commonly used materials are synthetic polymers. Examples of those are poly(lactic acid) (PLA), polyglygolide, poly(ε-caprolactone) (PCL), and their co-polymers, biodegradable glass, and poly(ethyleneterephthalate) (PTFE).

In three-dimensional (3D) cell culturing, a suitable culturing matrix should be able to mimic components of native ECM to provide a scaffold having similar properties with the native ECM, such as structural support for cells and a network of interconnected pores for efficient cell migration and transfer of nutrients to the cells.

Hydrogels, both of synthetic and natural origin, have recently emerged as suitable scaffolds for 3D cell culture. The network of interconnected pores in hydrogels allows retention of a large amount of biological fluid facilitating transport of oxygen, nutrients and waste. Furthermore, most hydrogels can be formed under mild cytocompatible conditions and their biological properties can be modulated by surface chemistry.

Engineered hydrogels with modified mechanical, chemical and biological properties have the potential to mimic the ECM and thus establish their utility in 3D cell culture. Commercial products for 3D cell culturing are for example cell culture matrices PuraMatrix™ (3DM Inc.) and Matrigel (BD Biosciences). PuraMatrix™ is a hydrogel of self-assembled peptide nanofibers which resembles the structure of natural fibrillar collagen in ECM with fiber diameter 5-10 nm. It has also high water content, typically 99.5%. U.S. Pat. No. 7,449,180 and WO 2004/007683 disclose peptide hydrogels. Matrigel is gelatinous protein mixture secreted by mouse tumor cells. The mixture resembles the complex extracellular environment found in many tissues and is used by cell biologists as a substrate for cell culture. MaxGel™ ECM Matrix (Sigma-Aldrich), which includes a mixture of human ECM components, forms a gel in ambient temperature.

Bacterial cellulose (BC) has been used in wound healing membranes and as a scaffold in cell culture. The limitation in the use of bacterial cellulose in cell culture is the inherent structure of the fermented material: upon cultivation, BC is formed as very tight membranes in air-water interphase in the fermenter. The formed membranes are too tight for 3D cell culturing and various modifications. If used as cell culture matrix, the porosity of the BC matrix has to be increased for adequate cell penetration and formation of cell clusters.

U.S. Pat. No. 5,254,471 discloses a carrier for cell culture comprising ultra-fine fibers. WO 2009/126980 discloses cellulose-based hydrogels whose framework substance consists essentially of or entirely of cellulose and are formed by regeneration from organic solvents. EP1970436B1 discloses carrier material for undifferentiated cell cultures. EP2633032B1 discloses plant derived cell culture and cell delivery compositions comprising cellulose nanofibers and/or derivatives thereof. EP2633033B1 relates to cell culture and cell delivery compositions comprising cellulose nanofibers and/or derivatives thereof based on microbial cellulose. U.S. Pat. No. 9,593,304B2 discloses materials for culturing and transporting stem cells in a 3D culture. The materials comprise nanofibrillar cellulose in a form of 3D continuous entities is a bio-compatible hydrogel.

Novel biomaterials and methods for culturing mammalian cells ex vivo are increasingly needed to study cell and tissue physiology and to grow replacement tissue for regenerative medicine e.g. in cell transplantations. Two-dimensional (2D) culture has been the paradigm for typical in vitro cell culture; however, it has been demonstrated that cells behave more natively when cultured in 3D environments. Permissive, synthetic hydrogels and promoting, natural hydrogels have become popular as 3D cell culture platforms; yet, both of these systems still possess limitations.

Nanofibrillar cellulose is feasible material for 3D cell culture. NFC hydrogel (GrowDex™, UPM-Kymmene, Helsinki, Finland) native nanofibrillar cellulose grade is especially suitable to support for example spheroid formation. However, cell types which naturally tend to expand and spread, i.e. take much space or is voluminous, like neural cells, do not grow optimally in reported nanofibrillar cellulose grade and cell growth is in some cases limited.

BRIEF DESCRIPTION OF THE INVENTION 2D neuronal cultures are easier to handle but do not mimic the in vivo situation in which cells interact with each other and with the surrounding environment as in 3D cultures, e.g., tissue-specific architecture is missing in 2D cultures (Geckil et al. 2010; Nisbet et al. 2008). Moreover, neuronal cells have a more complex morphology in 3D, and 3D structures may enhance the maturation and inhibit the proliferation of stem cell-derived neuronal cells. Thus, when in vivo mimicking in vitro models or cell products for transplantation therapies are developed, it is very important to study cells in 3D.

It was previously reported that anionic polymers may induce a supportive effect on neuronal cells (Hoffman 2002). The present inventors found that anionic nanofibrillar cellulose (aNFC) is more suitable hydrogel than native NFC hydrogel to support spreading and development of expanding cells. As an example, human neuronal cells have been cultured to form neural networks. The aNFC hydrogels were better for supporting neuronal cells, and especially for neurite outgrowth of single cells. This improvement is based on two hydrogel improvements: 1) anionic charge on the surface on nanofibrillar cellulose induced cell movement in hydrogels. Cells (especially neuronal) tend to sense charged groups in fibrils and spread along/towards extended fibrils. 2) Gel strength of anionic hydrogel is higher compared to native grade. Thus, cell culture can be performed in lower fibril concentration. The lower solid content enables more free movement of the cells and formation of protrusions in hydrogel as fibrils do not hinder the cell movement or e.g. neurite formation. Optimally solid content of aNFC is below 0.5 wt %, beneficially <0.4 wt %.

The present invention is directed to a composition for culture of expanding cells, said composition comprising plant-derived aNFC, in a form of hydrogel. More specifically, the invention is directed to a composition for culture of expanding cells, said composition comprising 0.05-0.5 wt % of plant-derived aNFC, in a form of hydrogel.

An aspect of the invention is a cell culture matrix, wherein the matrix comprises living cells and the composition for culture of expanding cells, said composition comprising 0.05-0.5 wt % of plant-derived aNFC, and the cells are present in said matrix in a 3D or 2D arrangement.

One aspect is a method for manufacturing a composition for culture of expanding cells, said composition comprising 0.05-0.5 wt % of plant-derived aNFC, in the form of hydrogel, said method comprising:
a. providing aNFC; and
b. mixing together said aNFC with water.

Another aspect is a method for 3D or 2D culturing of cells or tissues comprising providing a composition for culture of expanding cells, said composition comprising 0.05-0.5 wt % of plant-derived aNFC in the form of hydrogel, and inoculating at least one cell within the composition and culturing to obtain a cell mass, or in the form of matrix comprising living cells in a 3D or 2D arrangement that are cultured to obtain a cell mass.

According to another aspect the composition comprising 0.05-0.5 wt % of plant-derived aNFC, in a form of a hydrogel, is used for culturing expanding cells.

Characteristic features of the invention are presented in the appended claims.

DETAILED DESCRIPTION OF THE INVENTION

Figure 1:
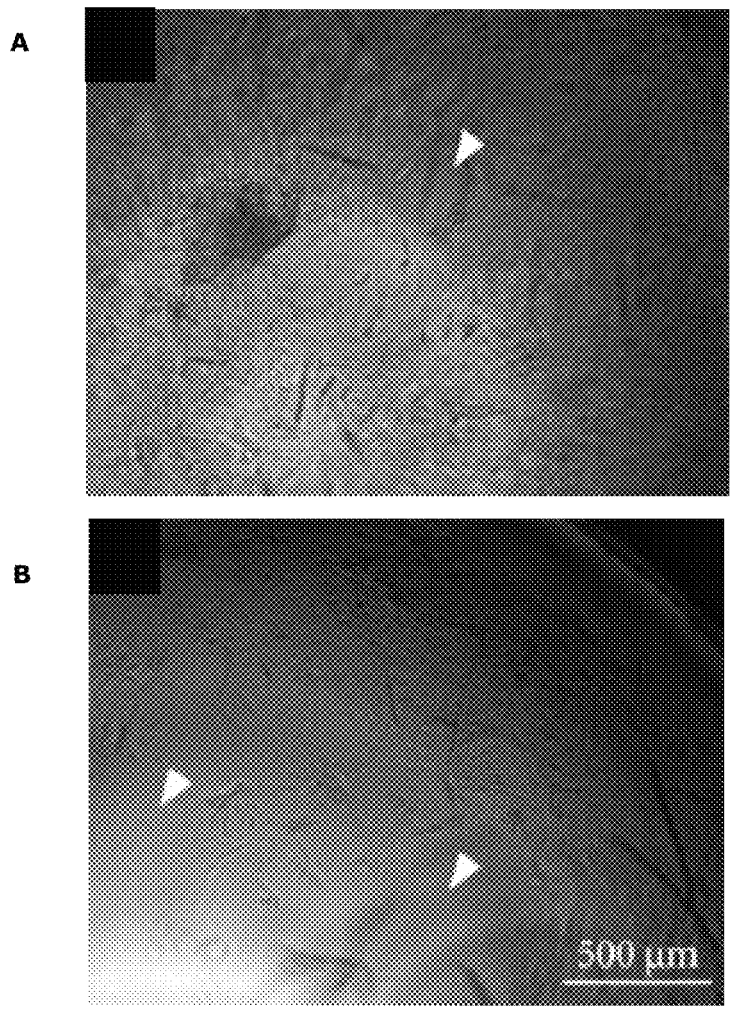
FIG. 1 shows classification of hydrogel loss in samples, moderate gel loss (A) and severe gel loss (B). White Arrow heads are showing areas with gel loss. Scale bar in images is 500 µm. Images are from aNFC 0.30% 60 µl sample.

Aspects of the present invention relate to cell culture compositions, 3D cell culture entities, and to methods of manufacturing and using the same in cell culture. Unless otherwise specified, the terms, which are used in the specification and claims, have the meanings commonly used in the cell culture. Specifically, the following terms have the meanings indicated below.

The term "cellulose pulp" refers to cellulose fibrils, which are isolated from any plant based cellulose or lignocellulose raw material, using chemical, mechanical, thermo-mechanical, or chemi-thermo-mechanical pulping processes, for example kraft pulping, sulfate pulping, soda pulping, organosolv pulping. The cellulose pulp may be bleached using conventional bleaching processes.

The term "native cellulose pulp" or "native cellulose" refers here to any cellulose pulp, which has not been chemically modified after the pulping process and the optional bleaching process.

The term "plant-derived" or "plant-derived cellulose material" may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Plant-derived non-wood materials may be for example from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed, or mixtures of these.

The term "mechanically disintegrated" refers here to that to obtain nanofibrillar cellulose, mechanical disintegration of cellulose pulp or oxidized cellulose raw material is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated nanofibrillar cellulose is used.

Several different grades of nanofibrillar cellulose have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final nanofibrillar cellulose product. Typically, non-ionic or native grades have wider fibril diameter while the chemically modified grades are much thinner and have a continuous network. The number average fibril diameter of the cellulose nanofibril is suitably from 1 to 200 nm, preferably the number average fibril diameter of native grades is from 1 to 100 nm, and in chemically modified grades from 1 to 20 nm. Size distribution is also narrower for the modified grades. For cell culture applications the nanofibrillar cellulose is preferably non-toxic to cells.

As used herein, the term "nanofibrillar cellulose" is understood to encompass nanofibrillar structures liberated from plant based cellulosic materials, such as cellulose pulp from hardwood or softwood. The nomenclature relating to nanofibrillar cellulose is not uniform and there is an inconsistent use of terms in the literature. For example, the following terms may have been used as synonyms for nanofibrillar cellulose: cellulose nanofiber (CNF), nanofibril cellulose, nanofibrillated cellulose (NFC), nano-scale fibrillated cellulose, microfibrillar cellulose, cellulose microfibrils, microfibrillated cellulose (MFC), and fibril cellulose. The smallest cellulosic entities of cellulose pulp of plant origin, such as wood, include cellulose molecules, elementary fibrils, and microfibrils. Microfibril units are bundles of elementary fibrils caused by physically conditioned coalescence as a mechanism of reducing the free energy of the surfaces. However, here the term "nanofibrillar cellulose" or NFC refers to a collection of cellulose nanofibrils liberated from cellulose pulp or cellulosic material, particularly from the microfibril units. Their diameters may vary depending on the source. A cellulose nanofibril typically has a high aspect ratio: the length exceeds one micrometer while the diameter is typically less than 100 nm. The smallest nanofibrils are similar to the so-called elementary fibrils, the diameter being typically in the range of 2-12 nm. The dimensions of the liberated nanofibrils or nanofibril bundles are dependent on raw material, any pretreatments and disintegration method. Intact, unfibrillated microfibril units may be present in the nanofibrillar cellulose. As used herein, the nanofibrillar cellulose is not meant to encompass non-fibrillar, rod-shaped cellulose nanocrystals or whiskers.

The term "anionic nanofibrillar cellulose" or "aNFC" refers to nanofibrillar cellulose, which has been chemically derivatized i.e. chemically modified to render the nanofibrillar cellulose anionic by introducing negative charges on the surface thereof. For the plant-derived aNFC of the invention, the chemical derivatization is carried out before the production of NFC, i.e. before the mechanical disintegration of the cellulosic raw material.

The nanofibrillar cellulose of the present invention is aNFC. The aNFC is obtained through anionization. Anionization is an example of chemical derivatization, i.e. a chemical modification. Anionization, or producing aNFC, is a modification to render the nanofibrillar cellulose anionic by introducing negative charges on the surface thereof. One example of anionization is anionizing by TEMPO ((2,2,6,6-tetramethylpiperidin-1-yl)oxyl) oxidation. Other examples are carboxymethylation and sulphonation. The reactions are performed as a pretreatment of cellulose pulp or other cellulosic raw material, before mechanical disintegration or liberated of the nanofibrils in other ways. The outcome of the processes is a charged aNFC. Typically, all of the raw material is modified and possible amounts of non-modified cellulose are insignificant.

According to one embodiment, the plant-derived anionic nanofibrillar cellulose comprises carboxymethylated or sulphonated nanofibrillar cellulose.

The nanofibrillar celluloses particularly suitably for use in the present invention are selected from plant-derived aNFCs and/or any combinations of different aNFCs. Typically, the aNFC used in the present invention are native celluloses which have been subjected to anionization, or alternatively modified celluloses which have been subjected to anionization.

Physical derivatization of cellulose to anionic cellulose may be performed by physical adsorption of anionic substances on the cellulose surface.

Derivatized grades are typically prepared from bleached cellulosed pulps. Any hemicelluloses present may also be derivatized in the derivatized grades of NFC.

Examples of production of nanofibrillar cellulose has been described for example in EP2782937A1, where carboxymethylation is described, and in WO 2015/015056, where oxidation is described.

Derivatized grades of nanofibrillar cellulose usually have smaller nanofibril diameter and narrower size distributions than native or non-derivatized grades of nanofibrillar cellulose.

The smaller the nanofibrils size, the larger is the surface area and thus the effective charged surface. When cellulose has been derivatized, it is more labile and easier to disintegrate. Generally, the smaller nanofibril sized accomplished through the anionic derivatization is beneficial for the present invention.

The derivatized nanofibrillar celluloses are typically thinner than native nanofibrillar celluloses. The number average diameter for nanofibrils of plant-derived aNFC may vary between 2 and 200 nm, or between 2 and 100 nm. Preferably, the number average diameter for plant-derived aNFC is 2-20 nm or 2-10 nm, more preferably 3-6 nm. The smallest nanofibrils are similar to so called elementary fibrils, which are typically 2-12 nm in diameter. The above values are estimated from Cryo-TEM images. The dimensions of the nanofibrils or nanofibril bundles are dependent on raw material and disintegration method. The length of a nanofibril is somewhat challenging to measure accurately. The plant-derived aNFC typically have nanofibril length varying between 0.3 and 50 micrometers or 0.3 and 20 micrometers. Preferably, the length is 0.5-20 micrometers or 0.5-10 micrometers, and more preferably 1-10 micrometers or 1-5 micrometers. The length depend on the anionization method used. The above values are estimated from electron microscopy or AFM images.

The degree of fibrillation can be evaluated from fibril analysis where the number of larger, only partially fibrillated entities, are evaluated. For the plant-derived anionic nanofibrillar cellulose the number of those unfibrillated particles per mg of dry sample varies from 1 to 10 000, preferably between 1 and 5000, most preferably between 1 and 1000. The fibril analysis may suitably be carried out using FiberLab analysis method.

Nanofibrillar cellulose form hydrogel structures with a desired viscosity when dispersed in an aqueous medium, such as water. Any suitable mixing or blending apparatus may be used to form the hydrogel.

The rheology of plant-derived nanofibrillar cellulose hydrogels show reversible gelation. At high stress levels a fluid-like behavior is observed whereas at low stress levels and quiescent conditions a step-wise transition to solid-like behavior occurs. Since a change in the environment does not trigger conformational changes of the polymer chains of the nanofibrillar cellulose hydrogel, the gel strength is almost constant over very broad temperature, pH, or ionic strength ranges.

The stiffness of the nanofibrillar cellulose hydrogels can be evaluated from viscoelastic measurements of the gels. The stiffness of the nanofibrillar cellulose hydrogels reflects also ease of spreading of the hydrogels. When the viscosity is plotted as function of applied shear stress, a dramatic decrease in viscosity is seen after exceeding the critical shear stress (loss modulus, G">storage modulus, G', and thus, a loss tangent is >1).

Tissues are viscoelastic and are made up of cells and ECM. Matrix stiffness or strength is one of the many mechanical forces acting on cells and is appreciated as an important mediator of cell behavior. It regulates cell signaling and has an effect e.g. on growth, survival, cell alignment and motility. The optimal stiffness varies widely for different kinds of cells. For example, different types of liver cells have been reported to response in different ways to matrix stiffness.

It has also been demonstrated that the stiffness of individual collagen fibrils can be varied reproducibly and has a significant impact on cell phenotype.

Furthermore, cells are known to mechanosense over relatively short distances, roughly the width of an adjacent cell. Therefore, in a tissue, a cell is unlikely to sense mechanical forces beyond its near neighbor. Further, the cells that make up tissues are adherent, attached to some combination of their neighboring cells and surrounding ECM. Most cells, but not all, require adhesion for survival.

Nanofibrillar cellulose has been reported to function well as a cell culture matrix. It is believed that the network of cellulose nanofibrils mimics ECM supporting cell survival and proliferation. The stiffness of the nanofibrillar cellulose hydrogels can be easily adjusted by dilution.

The present nanofibrillar cellulose has properties, which enable optimal matrix for culture of cells and tissues.

There have been difficulties in maintaining and growing cells in all the thicknesses of hydrogels. In the present invention the maintenance and growth conditions or cells are improved. The present nanofibrillar cellulose and hydrogel thereof provide optimal stiffness or strength and optimal thickness In the present invention the amount of required nanofibrillar cellulose may be smaller than previously for achieving the desired stiffness.

The nanofibrillar cellulose may have storage modulus between 1 and 40 Pa, preferably between 3 and 30, more preferably between 5 and 20, when dispersed to a concentration of 0.5 w % in water.

According to one embodiment the plant-derived aNFC has a loss tangent more than 1 when the range of storage modulus is between 1-20 Pa, preferably 2-10 Pa, when dispersed to a concentration of 0.5 w % in water.

A loss tangent of the present nanofibrillar cellulose is less than 0.3, preferably less than 0.25, when a shear stress is less than 0.5 Pa.

According to one embodiment of the invention the plant-derived aNFC comprises nanofibrillar cellulose manufactured from oxidized cellulosic raw material having a carboxylate content above 0.75 mmol/g, preferably 0.75-1.6 mmol/g, more preferably 0.9-1.2 mmol/g based on the weight of the cellulosic raw material.

According to one embodiment of the invention the plant-derived aNFC is of cellulose I (cellulose crystal I form). According to another embodiment the plant-derived aNFC can comprise other cellulose forms also. Several different crystalline structures of cellulose are known. The structures correspond to the location of hydrogen bonds between and within strands of the cellulose. Natural cellulose is cellulose I. Cellulose in regenerated cellulose fibrils is cellulose II. Cellulose of higher plants consists mainly of the substructure cellulose $I_\beta$.

According to one embodiment the plant-derived aNFC is TEMPO oxidized nanofibrillar cellulose. The plant-derived aNFC may be obtained by a TEMPO oxidation process comprising the steps of firstly, oxidizing primary alcohols of cellulose to aldehydes and carboxylic acids through TEMPO oxidation by using sodium hypochlorite as the main oxidant to obtain oxidized cellulose with a certain carboxylate content, and thereafter fibrillating the oxidized pulp to obtain aNFC. The plant-derived aNFC of the invention may be TEMPO oxidized nanofibrillar cellulose having aldehyde groups in an amount of less than or equal to 0.3 mmol/g, preferably less than or equal to 0.2 mmol/g, more preferably less than or equal to 0.15 mmol/g by dry weight of the nanofibrillar cellulose.

The chemical composition or modification of nanofibrillar cellulose is commonly described as the degree of substitution (DS). Derivatization by anionization of the cellulose raw material used in the present invention is conducted to certain degree of substitutions levels prior to fibrillation/mechanical disintegration. The degree of substitution in the chemical derivatization process can vary broadly.

According to one embodiment of the invention the plant-derived aNFC comprises nanofibrillar cellulose manufactured from anionized cellulosic raw material having a degree of substitution (ds or DS) of at least 0.08. The degree of substitution for the plant-derived aNFC is typically between ds levels 0.08 and 0.3. Preferably, the degree of substitution for the plant-derived aNFC is between 0.1 and 0.25, or more preferably between 0.12 and 0.2. The degree of substitution may for example be 0.10, 0.11, 0.12, 0.13, 0.14, 0.15, 0.16, 0.17, 0.18 or 0.19. These specific ds levels were found to be advantageous in the present invention, because with these ds levels the anionic nanofibrillar cellulose obtained after mechanical treatment has optimal properties. A hydrogel of good quality was obtained having high viscosity and high aspect ratio. In addition, the energy needed for grinding was kept on a moderate level.

According to one embodiment of the invention the plant-derived aNFC comprises nanofibrillar cellulose manufactured from carboxymethylated cellulosic raw material having a degree of substitution above 0.1, preferably between 0.1 and 0.3, more preferably between 0.12 and 0.2.

The plant-derived aNFC cellulose may be obtained from cellulose material originating from plant based cellulose or lignocellulose raw material, using chemical, mechanical, thermo-mechanical, or chemi-thermo-mechanical pulping processes. According to one, non-limiting embodiment, the cellulosic raw material does not comprise regenerated cellulose fibrils, wherein the cellulose is cellulose II and/or recycled fibrils.

According to one, non-limiting, aspect the plant-derived aNFC is none mercerized nanofibrillar cellulose.

"A hydrogel" or "gel" or "nanofibrillar cellulose hydrogel" refers to aqueous dispersion of nanofibrillar cellulose having a homogeneous and continuous gel structure. The hydrogel can be formed by combining nanofibrillar cellulose with e.g. water, buffer solution or cell culture medium or any other aqueous solution optionally supplemented with additives. The term "hydrogel" in connection with nanofibrillar cellulose refers to a form where an aqueous dispersion of the nanofibrillar cellulose has a loss tangent less than 1. Hydrogel is a polymeric material that exhibits the ability to swell and retain a significant fraction of water within its structure, but it does not dissolve in water. NFC hydrogels are formed spontaneously without formation of covalent bonds; therefore, their strength can be easily altered e.g. by dilution. The NFC hydrogel has good suspending capacity. The NFC hydrogel is so-called reversible or physical gel involving physical cross-linking by entanglement of fibrils. The interactions in the network can be disrupted by application of stress, so NFC hydrogels have shear-thinning behavior. The viscoelastic properties of plant-derived nanofibrillar cellulose hydrogel scaffold differs considerably from nanofibrillar cellulose from other sources, such as from bacterial cellulose scaffolds.

A nanofibrillar cellulose of the present invention has a turbidity of 20 NTU or less, preferably 10 NTU or less, more preferably 6 NTU or less. The turbidity may be between 20 and 1 NTU, more preferably between 10 and 1 NTU, such as 9, 8, 7, 6, 5, 4, 3, 2 most preferably between 6 and 1 NTU in water at concentration of 0.1 w %.

According to one aspect the nanofibrillar cellulose has a turbidity of 20 NTU or less, preferably 10 NTU or less, more preferably 6 NTU or less, preferably the turbidity is between 20 and 1 NTU, more preferably between 10 and 2 NTU, in water at concentration of 0.1 w %.

Turbidity may be measured quantitatively using optical turbidity measuring instruments. There are several commercial turbidometers available for measuring quantitatively turbidity. In the present case, the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

The final product has excellent gelling properties and transparency as well as homogenous structure. The transparency is due to lack of fibril bundles, which results in a homogenous structure. The transparency of the final nanofibrillar cellulose hydrogel enables optical detection of cells with light microscopy due to lower light scattering. Additionally, no autofluoresence originates from nanofibrillar cellulose. Therefore, the nanofibrillar cellulose of the present invention has improved imaging properties. Use of the present nanofibrillar cellulose and hydrogel enables 3D imaging, which has not been possible previously.

The crystallinity of the present nanofibrillar cellulose may vary from 60% to 80%, preferably from 65 to 75%. The crystallinity may be for example 60%, 61%, 62%, 63%, 64%, 65%, 66%, 67%, 68%, 69%, 70%, 71%, 72%, 73%, 74%, 75%, 76%, 77%, 78%, 78%, 79%, or 80%.

Term "dispersion" in connection with nanofibrillar cellulose encompasses both hydrogels of nanofibrillar cellulose but also more dilute aqueous system not fulfilling the above requirement related to hydrogel. A dispersion is a system in which particles are dispersed in a continuous phase of a different state than the particles themselves.

"An aqueous medium" refers to any aqueous medium such as water, deionized water, buffer solution, or nutritional medium suitable for maintaining, transporting, isolating, culturing, propagating, passaging or differentiating of cells or tissues. The aqueous medium may further contain various additives such as special extracellular matrix components, serum, growth factors, antibiotics, preservatives, peptides and proteins. As known in the art, the choice of the cell culture media depends on the cell type to be cultured. Many commercial cell culture media exist that support undifferentiated or differentiating growth of cells. Examples of cell culture media suitable in the present invention include mTeSR1 (StemCell Technologies), mesenchymal stem cell media (Lonza, Walkersville, MD, # PT-3001), STEMPRO hESC SFM (Invitrogen), Williams' E (Invitrogen) and differentiation media.

"Suspended" or "suspension" when used in context of 3D entity or hydrogel bodies refers to a heterogeneous mixture of an aqueous medium and hydrogel wherein the hydrogel may be present as separate or interconnected hydrogel bodies.

The term "cell culture matrix" refers to a system comprising cells and/or tissue and the 3D entity, the cells and/or tissue being present at least partially embedded in said entity in a 3D or 2D arrangement. 3D and 2D in context of cell cultures refers to the way the cells are arranged, for example 3D may refer to cluster or spheroid-like arrangement and 2D to single or layered arrangement. Cell culture matrix refers also to material configured for cell culturing and providing a growth matrix that increases the available attachment surface for the adherence of the cells so as to mimic the infrastructure of the tissue.

The term "cell culture" or "culturing of cells" refers to maintaining, transporting, isolating, culturing, propagating, passaging or differentiating of cells or tissues. Cells can be in any arrangement such as individual cells, monolayers, cell clusters or spheroids or as tissue.

The term "expanding cell" refers to a cell, which naturally tends to expand, branch and spread, i.e. takes much space or is voluminous. Expanding cell may expand for example by growing protrusions or projections and/or using projections/ protrusions for moving for example in a matrix. Expanding cell may use protrusions or projections also for forming scaffolds or networks. Examples of expanding cells are neural cells which expand in a sense that they grow neurites. Dendritic branching is a multi-step biological process by which neurons form new dendritic trees and branches to create new synapses. Also endothelial cells, which form the linings of blood vessels and lymphatic vessels, can be considered as expanding cells. Many types of mammalian cells can aggregate and differentiate into 3D multicellular spheroids when cultured in suspension or a nonadhesive environment. The expanding cells move and expand instead of forming spheroids.

The term "neuronal cell" or "neuron" refers to the three major cell phenotypes of CNS, i.e. neurons, glia, and astrocytes. A "neurite" or "neuronal process" refers to any projection from the cell body of a neuron. This projection can be either an axon or a dendrite. The term "neurite outgrowth" refers to a key process during neuronal migration and differentiation. Complex intracellular signaling is involved in the initiation of neurite protrusion and subsequent elongation. The formation of complex neural circuits is heavily influenced by axon branching. Preferably, the cells used the invention are neuronal cells. The term "neuron-like cells" refers to cells that are not considered adult neurons. Neuron-like means that these cells share properties similar to neurons, e.g. releasing neurotransmitter by vesicles.

The term "endothelial cells" refers to vascular endothelial cells that are in direct contact with blood and to lymphatic endothelial cells that are in direct contact with lymph.

Derivative of nanofibrillar cellulose can be any chemically or physically modified derivate of nanofibrillar cellulose or nanofibril bundles. The chemical modification could be based for example on carboxymethylation, oxidation, esterification, or etherification reaction of cellulose molecules. The described modification can be carried out before, after, or during the production of nanofibrillar cellulose. Certain modifications may lead to NFC materials that are degradable in human body. A derivative may contain growth promoting proteins attached by covalent or weak bounds or with adsorption.

Microbial purity of the nanofibrillar cellulose and hydrogels containing them, is essential for the cell culture performance. Therefore, the nanofibrillar cellulose may be sterilized prior to cell culture experiments in a hydrogel form. In addition to that it is important to minimize the microbial contamination of the product before and during the fibrillation. Prior to fibrillation, it is advantageous to aseptically collect the cellulose pulp from the pulp mill immediately after bleaching stage when the pulp is still sterile.

Chemically, cellulose macromolecules are known to be very stable molecules. Hydrolysis of cellulose requires using harsh conditions and typically strong acids, like 56% sulphuric acid, are used.

The dimensions of individual cellulose nanofibrils of nanofibrillar cellulose are close to dimensions of collagen fibrils in ECM, i.e. 4-10 nm. Therefore, NFC based hydrogels can be used in 3D cell culture matrix.

In the cell culture experiments of the present invention, chemically modified aNFC forming optically transparent hydrogels is used. Detailed description of the materials is presented in the Examples, Materials and methods section. The concentration of aNFC in the hydrogel is adapted to a concentration suitable for the cell which is cultured. The concentration of the aNFC in the total volume may vary in the range 0.05-3% (w/v) depending on e.g. the cell type and cell line. In neuronal cell culture a range of 0.05-0.5% (w/v) may be used, such as w/v concentrations of 0.05, 0.055%, 0.06%, 0.065%, 0.07%, 0.075%, 0.08%, 0.085%, 0.09%, 0.095%, 0.1%, 0.15%, 0.2%, 0.25%, 0.3%, 0.35%, 0.4%, 0.45% or 0.5%. Preferably, the range is 0.05-0.35% (w/v).

The nanofibrillar cellulose or a derivative thereof of the present invention can comprise chemically or physically modified derivatives of a nanofibrillar cellulose or nanofibril bundles.

Nanofibrillar cellulose described in this invention is not the same material as so called cellulose whiskers, which are also known as: cellulose nanowhiskers, cellulose nanocrystals, cellulose nanorods, rod-like cellulose microcrystals or cellulose nanowires. In some cases, similar terminology is used for both materials, for example by Kuthcarlapati et al. (2008) where the studied material was called "cellulose nanofiber" although they clearly referred to cellulose nanowhiskers. Typically these materials do not have amorphous segments along the fibrillar structure as cellulose nanofibrilils, which lead to more rigid structure. Cellulose whiskers are also shorter than cellulose nanofibrilils; typically the length is less than one micrometer.

The term "article for cell culture" refers to any article suitable for cell culture including single and multi-well plates, such as 6, 12, 96, 384, and 1536 well plates, jars, petri dishes, flasks, multi-layered flasks, beakers, plates, roller bottles, slides, such as chambered and multichambered culture slides, tubes, cover slips, bags, membranes, hollow fibers, beads and microcarriers, cups, spinner bottles, perfusion chambers, syringes, bioreactors, and fermenters.

The term "shaping" refers to shaping a composition, optionally in or on a secondary material. Shaping can be done by 3D-printing, spinning, spraying, dropping, spreading, coating or impregnation with concomitant or subsequent cross-linking, preferably shaping the composition directly into cross-linking conditions or chemical.

The term "shaped matrix" refers to matrix, which is in a shape such as a wire, a 3D cord, a tube, a mesh, a bead, a sheet, a web, a coating, an interlayer, or an impregnate.

The term "co-culture" refers to a cell culture wherein more than one different cell types are cultured in the same culture matrix simultaneously. The co-culture enables different cell types to be utilized in a single treatment system. In the present invention at least two cell types of different origin can be cultured as a co-culture.

The term "printing" refers to a process of producing structures and patterns comprising aNFC as a printed material by means of 3D printing, laser assisted printing, extrusion, molding or electrospinning.

The present composition for cell culture, cell culture matrix or article may further comprise suitable additives selected from the group consisting of nutrients, buffering agents, pH indicators, extracellular matrix components, serum, growth factors, antibiotics, preservatives, peptides and proteins.

Depending on the cell line and the intended use of the cultured cell, the culturing may be carried out 2D or 3D. The cells are dispersed or inoculated on or in the 3D entity or article allowing 2D or 3D growth of cells on the hydrogel bodies and penetration of the propagating cells and extracellular structures of the cultured cells inside the hydrogel bodies.

According to one embodiment the cells obtained from a cell culture containing the present composition can be used for example for preparation of central nervous system disease cell models, for 3D printed structures, especially for neuronal cells, for treating spinal cord injuries, for diagnosing Alzheimer's disease or Parkinson's disease, or for drug testing in a cell culture.

The removal of cellulose nanofibrils can be carried out for example with enzymes mixtures comprising all necessary enzymes for total degradation of cellulose molecules as well as other wood derived components in it, such as hemicelluloses. Proper enzymes are for example designed enzyme mixtures for the NFC in question and commercially available cellulase-hemicellulase preparations. The composition of the mixture can vary depending on the chemical composition of the raw material used for production of that NFC. For example when birch pulp is used for production of NFC the mixture includes at least intact endo- and exocellulases or parts of them, endo-xylanases and β-D-glycosidases and 8-D-xylosidases. For hydrolysis of softwood derived NFC the mixture needs to be supplemented at least with endo-mannanases and β-D-mannosidases. The benefit of designed mixtures pooled from purified enzyme components is that they do not contain additional proteins or other unwanted components, such as side activities, debris from the cultivation organism or residues from culture broth, which is often the case for commercial enzyme preparations. Especially harmful is, if the preparation contains proteases, which might attack on the cultured cell surfaces. Commercial enzyme mixtures designated for total hydrolysis of plant based materials can also be used in hydrolysis of NFC, but more preferably after at least crude purification step, such as gel filtration or dialysis. Regardless of the enzyme preparation, either a designed or commercial mixture, the components are selected so that they can optimally hydrolyse NFC for example in respect of pH, temperature and ionic strength. Commercial preparations are available, which are acting either in the acidic pH values (pH 3.5-5) or basic pH values (pH 6-8) and at temperatures from room temperature up to 60-80° C. Very often the cells are grown at 37° C., which is an optimal temperature for the most cellulases and hemicellulases.

It is commonly known that certain enzymes, cellulases, are able to hydrolyse [beta]-(1-4)-bonds in cellulose. For example endo-1,4-p-glucanases (EGs) that target cellulose chains in random locations away from the chain ends; exoglucanases or exocellobiohydrolases (CBHs) that degrade cellulose by splitting off molecules from both ends of the chain producing cellobiose dimers; and [beta]-glucosidases (BGLs) that hydrolyze the oligosaccharides produced and cellobiose units (produced during EG and CBH attack) to glucose. Respectively, cellulose nanofibrils can be enzymatically hydrolyzed to glucose with an aid of cellulases (Ahola, et al. 2008). Total hydrolysis of NFC to monomeric sugars necessitates that the enzyme mixture contains also endo acting hemicellulases, such as xylanases and mannanases, and β-D-glycosidases, β-D-xylosidases and -D-mannosidases. When only partial hydrolysis is aimed, for example to reduce the viscosity of hydrogel, composition of the enzyme mixture can be tuned to include excess endoglucanases and less or no cellobiohydrolases. In the latter case hemicellulases can be included into the mixture since they enhance hydrolytic action of cellulases. Enzymatic hydrolysis of cellulose can be utilized in cellulose nanofibril containing cell culture systems for various reasons. Upon the hydrolysis of NFC hydrogel, the viscosity of the media is drastically lowered and the cultured cell structures are easily accessible e.g. for staining. Also, after the hydrolysis, the cell structures can be transferred or transplanted without the cellulose containing material. The degradation product, glucose, is generally non-toxic to cells and can be utilized as a nutrient in cell culturing.

In case enzymatic hydrolysis, e.g. with a cellulase, is used in breaking the NFC (including aNFC) hydrogel, the enzyme may be inactivated or removed from the cell culture system. A skilled person is readily able to select any appropriate method to inactivate or remove the enzyme. Examples of suitable methods include inactivation by inhibitors or neutralizing antibodies, and removal of the cellulase by washing, filtration, affinity purification, or any other method which is suitable for the selected application. Inactivation or removal of the enzyme prevents presence of an active enzyme which is able to break the NFC gel structure in case the cells are cultured in a NFC based matrix after the enzyme treatment. Removal of the enzyme may also be required in certain downstream applications of the cultured cells.

According to one preferred embodiment, the composition is enzymatically treated with a cellulase for a time sufficient to at least partly release cell mass. According to another preferred embodiment, the cellulase is inactivated or removed from the cell mass after enzymatic treatment.

Differentiation of cells can be monitored following expression of any marker gene known in the art. For example early or late markers can be used depending e.g. on specific application and the cell type.

The aNFC hydrogel of the present invention is "a direct product of homogenization of said cellulose nanofibrils", e.g., by high pressure homogenization of wet cellulose pulp fibrils. In an aqueous environment, cellulose nanofibrils according to the present invention form a continuous hydrogel network of dispersed nanofibrils or nanofibril bundles. The gel is formed by highly hydrated fibrils that are entangled between each other, even at very low concentrations. The fibrils may interact also via hydrogen bonds. Stable hydrogels with as low as 0.3-0.5 wt % cellulose nanofibrils (produced by mechanical disintegration) can be formed without addition of any suspending or thickening agents. Indeed, the direct product from the process is a dilute nanofibrillar cellulose hydrogel. A transparent NFC hydrogel is obtained by similar homogenization process of a chemically modified (TEMPO-oxidized) cellulose pulp.

Not all microfibrillated celluloses behave in the same manner just by virtue of falling into the category of "microfibrillated cellulose." That is, not all microfibrillated celluloses have identical properties and features. Moreover, the process by which the microfibrillated celluloses are made significantly affects the properties of the end product. Therefore, that the cellulose is mechanically disintegrated, has a particular meaning and effect on the resulting cellulose nanofibril structure.

CONCLUSIONS

It was previously reported that anionic polymers may induce a supportive effect on neuronal cells. The present inventors found that hydrogel made of aNFC is more suitable to support spreading and development of expanding cells. As an example, the present inventors cultured human neuronal cells to form neural networks. The aNFC hydrogels were better for supporting neuronal cells, and especially the neurite outgrowth of single cells. This improvement as compared to prior art hydrogels is based on two hydrogel improvements: 1) anionic charge on the surface on nanofibrillar cellulose induced cell movement in hydrogels (because cells tend to sense charged groups in fibrils and spread along/towards extended fibrils) and 2) gel strength of anionic hydrogel is higher compared to native grade (because fibril diameter and size is smaller and number of nanofibrils is higher in same solids content). Thus, cell culture can be performed in lower fibril concentration. The lower solid content enables more free movement of the cells in hydrogel as fibrils do not hinder the movement. Optimally solid content of aNFC is below 0.5 wt %, beneficially <0.4 wt %.

EXAMPLES

The following examples are illustrative of embodiments of the present invention, as described above, and they are not meant to limit the invention in any way.

Example 1. Testing Nanofibrillar Cellulose Based Hydrogels with Human Neuronal Cells

Materials and Methods

Human neuronal cells were cultured 2 weeks as encapsulated within the nanofibrillar cellulose-based hydrogels. Cells used in experiments were human neurons, pre-differentiated from human embryonic stem cell line Regea 08/023 (Lappalainen et al. 2010; Ylä-Outinen et al. 2014). Briefly, the differentiation of hESCs to neural cells was performed by transferring hESC clusters containing approximately 3000 cells into six well ultra-low attachment plates (Nunc, Thermo Fisher Scientific, Rochester, NY, USA) and culturing the cells as floating aggregates, neurospheres, in neural differentiation medium containing 1:1 DMEMedium/F12 (Gibco, Invitrogen, Finland) and neurobasal medium supplemented with 2 mM GlutaMax™, 1×B27, 1×N2 (Gibco), 20 ng/ml fibroblast growth factor (bFGF, R&D Systems, Minneapolis, MN, USA) and 25 U/ml penicillin/streptomycin (Cambrex, Belgium). The medium was changed three times per week and the spheres were mechanically dissected once a week. Neurospheres were cultured for eight weeks to gain pure neuronal population.

The Preparation of Anionic NFC

The aNFC was prepared from bleached cellulose pulp by high pressure homogenization using industrial fluidizer for fibrillation. The raw material was aseptically collected from a pulp mill and thoroughly purified prior to the homogenization with sterilized machinery. Thus, the microbial purity was maintained through the whole production process. The purified was anionically modified prior to the fibrillation. The anionic modification is based on oxidation of cellulose pulp. Due to the modification, the cellulose pulp is easy to disintegrate to cellulose nanofibrils. Also, the labilization reaction brings aldehyde and carboxylic acid functionalities on the surface aNFC, which increases the hydrophilicity of the material. WO 09/084566 and JP 20070340371 disclose such modifications. The oxidized cellulose pulp was thoroughly purified after the chemical modification. The purified fibrils were diluted with sterilized, ultra-high quality water before the fibrillation. The NFC concentration of the resulting hydrogel is typically 1-2 wt %. The NFC hydrogel was autoclaved (121° C./20 min) directly after fibrillation.

TABLE 1

Abbreviations of the hydrogels used and corresponding sample numbers.

| Hydrogel type | Sample number |
| --- | --- |
| Growdex 1.50% | 1 |
| Growdex 1.00% | 2 |
| aNFC 0.65% | 3 |
| aNFC 0.45% | 4 |
| aNFC 0.30% | 5 |
| Laminin coating (2D control) | 6 |
| PuraMatrix (3D control) | 7 |

Osmotic Balancing

Prior to cell culture experiments, the hydrogel material was incubated in presence of cell culture media for 5 hours in room temperature for balancing osmotic environment. Hydrogels were pipetted to 500 µl-1 ml aliquots into 2 ml Eppendorf tube with round bottom. 1 ml of cell culture medium was slowly added on top of the hydrogels. After incubation, tubes were centrifuged (5 min, 1500 rpm) and excess medium (~1 ml) on top was removed.

Cell Encapsulation

Pre-differentiated neurospheres were collected to Eppendorf tubes and cell culture medium was removed. Cells were enzymatically dissociated using Tryple Select (Invitrogen, 12563-011) to form suspension with small cell aggregates and single cells. Amount of cells and viability in suspension was calculated using Countess-cell counter (Invitrogen) with trypan blue (1:1). Cell density used was 5 million cells per 1 ml of hydrogel. Calculated amount of cell suspension was pipetted to Eppendorf tube, centrifuged (5 min, 1500 rpm) and cell culture medium was removed. Cell pellet was resuspended to 50 µl of fresh cell culture medium and pipetted as small droplets inside the hydrogel (750 µl). Cells were mixed with the hydrogel by slowly pipetting up and down as well as stirring with pipet tip until the mixture seemed homogenous. After that the mixture was aliquoted to 96-well plate wells. 150 µl of cell culture medium was added on top of the cultures.

Preparing of laminin coated 2D and PuraMatrix encapsulated 3D control samples was performed as previously published (Ylä-Outinen et al. 2014).

Cell Culture

Cells were cultured for two weeks as encapsulated within the hydrogel. The used culture medium was neural differentiation medium (NMD) containing 1:1 DMEM/F12:neurobasal medium, supplemented with 2 mM GlutaMax™, 1×B27, 1×N2 and 25 U/ml penicillin/streptomycin. 100 µl of the cell culture medium was changed three times a week. Cultures were monitored with phase contrast microscope. Stability of hydrogels during cell culture was evaluated visually. The cultures for confocal imaging were performed in MatTek 96-well plates with No. 1.5 glass bottom, Part No: P96G-1.5-5-F.

Immunocytochemical Analysis, Imaging and Image

Immunocytochemical analysis was performed as previously published (Koivisto et al. 2017). Primary antibodies used were Anti-Microtubule-Associated Protein 2 (MAP2) (AB5622, Merck Millipore, Germany) and Monoclonal Anti-β-Tubulin III antibody (T8660, Sigma-Aldrich Finland Oy, Finland). After staining the cultures were imaged with an Olympus IX51 inverted microscope with Olympus DP30BW digital camera (Olympus Corporation, Japan) with 4× objective. Greyscale images were processed using Adobe Photoshop CS4 (version 11, Adobe Systems Inc. CA).

Detailed confocal 3D image stacks were taken with Zeiss LSM 780-confocal unit mounted into inverted Cell Observer microscope (Carl Zeiss, Germany) using 25× (N.A.=0.80, Zeiss LD LCI Plan-Apochromat, Carl Zeiss) objective with glycerin. The confocal data was deconvoluted using Huygens Essential-software (Huygens compute engine 15.10.1p5 64b, Scientific Volume Imaging (SVI, Netherlands) and visualized with ImageJ (Version 1.39, U. S. National Institutes of Health, USA).

Results

General Overview of the Experiment

Sample preparation, hydrogel dilutions, cell plating and cell culture were successful with both studied hydrogels (Growdex and aNFC). All tested hydrogels supported neuronal survival and growth for two weeks. Sample preparation for imaging was also successful although some amount of gel loss occurred. Both studied hydrogels had good visual properties in fluorescence imaging and the aNFC hydrogels were also highly suitable for phase contrast imaging due to transparency.

Hydrogel Handling in Preparation of 3D Cultures

The handling of Growdex hydrogel was very similar to our previous experiments (reported to UPM earlier). The Growdex material is slightly difficult to pipet and mix to homogenous sample. Provided 1 ml low-retention pipette tips made handling easier. Also provided instructions to pipet cell suspension as droplets inside the hydrogel had positive effect on sample homogeneity.

In contrary to Growdex, the new aNFC hydrogels were very easy to pipet and mix. Compared to previous experiments, there was a significant improvement in hydrogel user-friendliness.

Neuronal Growth Inside the Hydrogels

Neuronal network formation was evaluated after the 2 weeks culturing period by immunocytochemical staining against neuronal markers. Samples were imaged using wide field fluorescence microscope with low magnification objective. Cultures were classified into three categories: good, moderate and poor neurite growth according to the amount of visible neurites (FIG. 1). Cell survival in all samples was good, even in cases were only poor neurite outgrowth was observed (visual analysis).

In general samples with smaller volume (60 µl) had better neuronal growth, which can be seen as decrease in amount samples with poor growth. Overall best results were seen with aNFC (0.30%).

TABLE 2

Percentage of samples (two different volumes) observed to have good, moderate or poor neurite growth after 2 weeks in culture. Neurite growth was determined after immunocytochemical analysis against neuronal markers MAP-2 and B-tubulin III. Presentative images of each case of the classification are in FIG. 1.

|  | Good neurite growth (%) | Moderate neurite growth (%) | Poor neurite growth (%) |
|---|---|---|---|
| Sample volume 80 µl | | | |
| Growdex 1.50% | 22 | 11 | 67 |
| Growdex 1.00% | 11 | 22 | 67 |
| aNFC 0.65% | 0 | 0 | 100 |
| aNFC 0.45% | 11 | 0 | 89 |
| aNFC 0.3% | 89 | 11 | 0 |
| PuraMatrix | 0 | 22 | 78 |
| Sample volume 60 µl | | | |
| Growdex 1.50% | 0 | 67 | 33 |
| Growdex 1.00% | 33 | 67 | 0 |
| aNFC 0.65% | 33 | 33 | 33 |
| aNFC 0.45% | 67 | 33 | 0 |
| aNFC 0.3% | 100 | 0 | 0 |
| PuraMatrix | 0 | 100 | 0 |
| Laminin coating | 100 | | |

According to these results it can concluded:
1. The lowest concentration of aNFC (0.30%) was the best composition for human neuronal cells.
2. Neural network formation is more stable in the smaller sample volume (60 µl).

Confocal Analysis of the 3D Cultures

For more detailed cellular network visualization the confocal imaging was used. All studied materials were compatible for the confocal analysis and no background or autofluorescence problems occurred. In minor amount of samples the antibody washout was incomplete which can be seen as bright dots in the hydrogel. Growdex hydrogels supported mainly outgrowth from cell aggregates whereas aNFC hydrogels supported also neurite growth of single cells.

Off note: The original size of single hydrogel block was Ø~5 µm and height (z)~3 µm. The confocal system cannot cover the whole block into one image. Thus, presented images are from smaller selected areas of the hydrogel blocks. Also, some very nice cell and network areas seen with wide field fluorescence imaging were not accessible with confocal imaging. These are well known limiting factors in confocal imaging systems.

Growdex 1.50%

Figure 3:
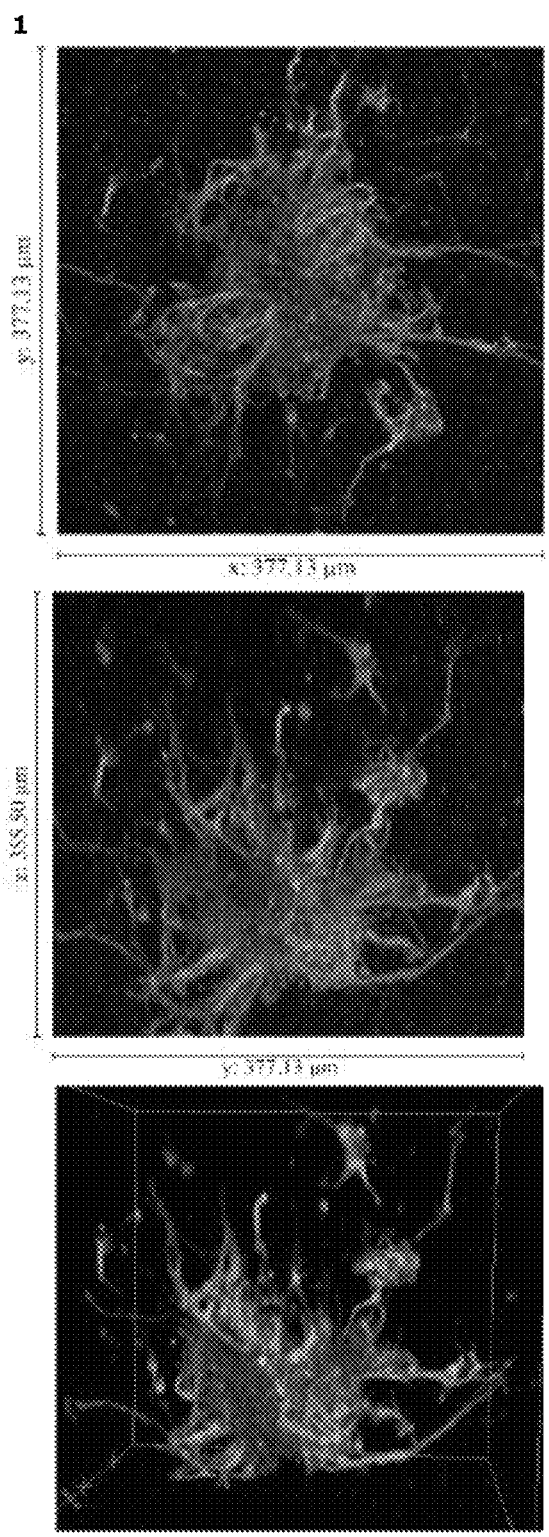
FIG. 3 shows confocal images from cell cultured as embedded within Growdex 1.50% hydrogel for two weeks. Three confocal stacks (1, 2 and 3) are presented as maximal intensity x-projection from top to bottom (A), maximal intensity projection from side and as 3D rendered visualization. In x*y plane the imaged area is 377.13 µm*377.13 µm in all images (A). The height of the confocal stack varies (z-direction, B). Both A and B images are in same scale. All presented images are from sample volume 60 µl. Markers in the images DAPI (blue), MAP-2 (green) and B-tubulin III (red).
Figure 3:
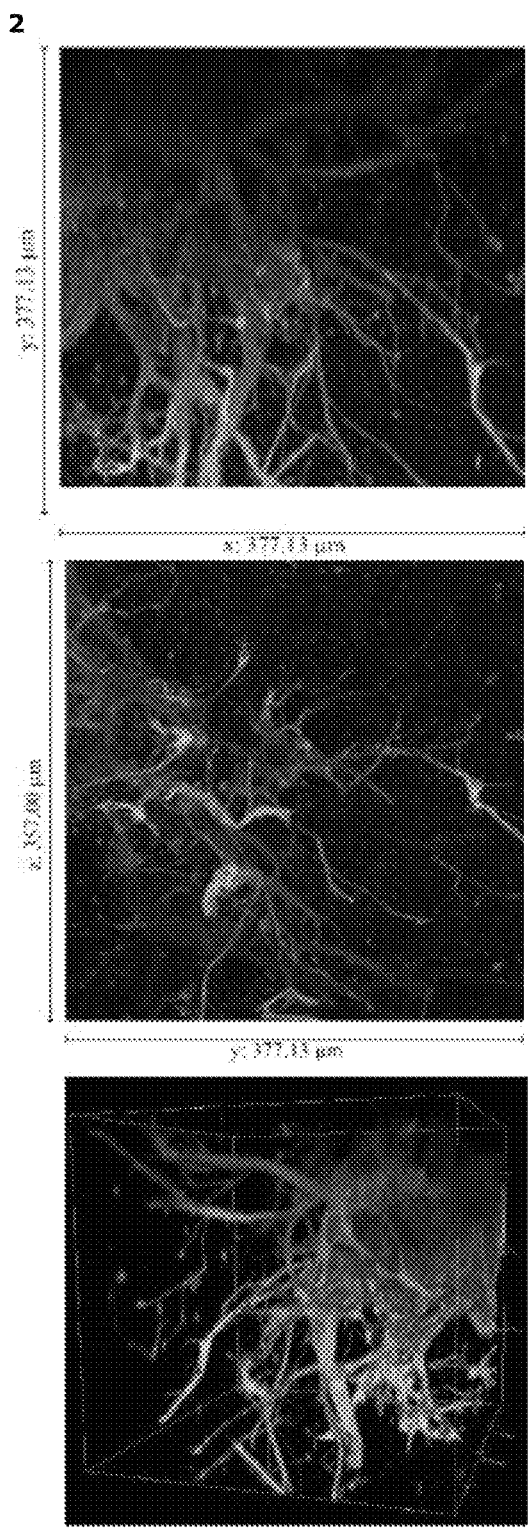
Figure 3:
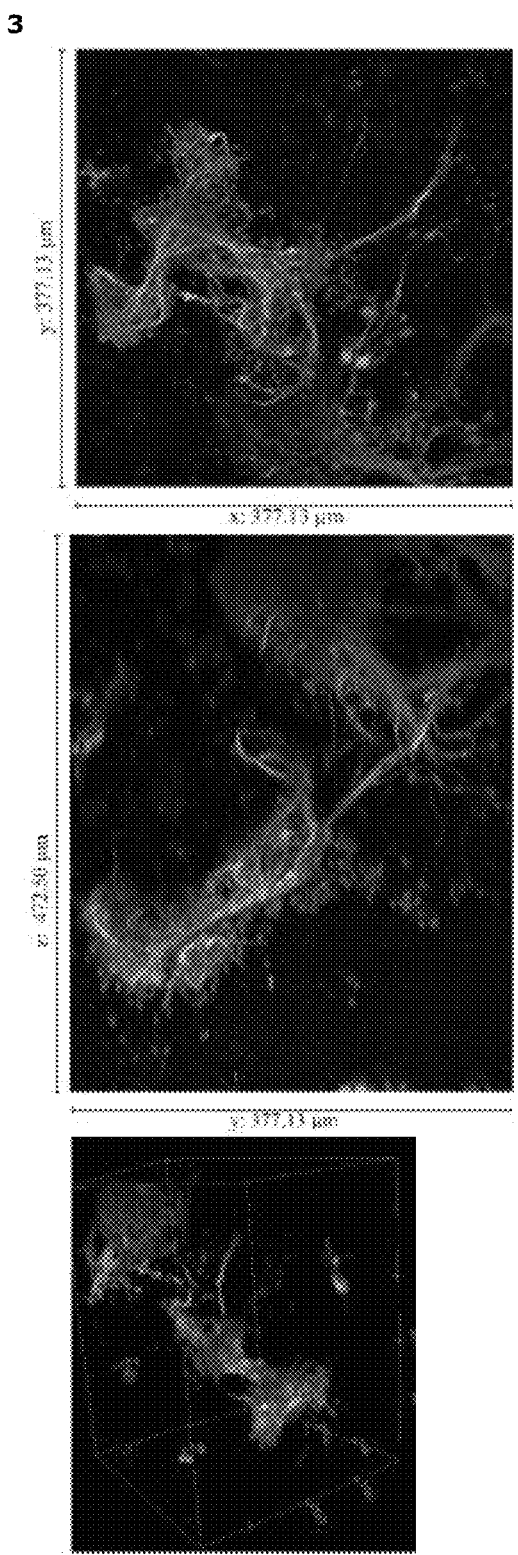

Massive neurite outgrowth was mainly seen from cell aggregates (FIG. 3, stacks 1 and 2). In some aggregates the amount of neurites was lower (FIG. 3, stack 3).

Growdex 1.00%

Figure 4:
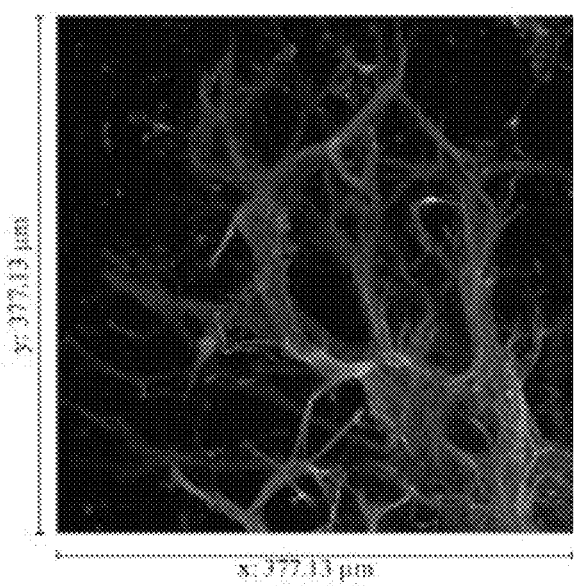
FIG. 4 shows confocal images from cell cultured as embedded within Growdex 1.00% hydrogel for two weeks. Three confocal stacks (1, 2 and 3) are presented as maximal intensity x-projection from top to bottom (A), maximal intensity projection from side and as 3D rendered visualization. In x*y plane the imaged area is 377.13 µm*377.13 µm in all images (A). The height of the confocal stack varies (z-direction, B). Both A and B images are in same scale. All presented images are from sample volume 60 µl. Markers in the images DAPI (blue), MAP-2 (green) and B-tubulin III (red).
Figure 4:
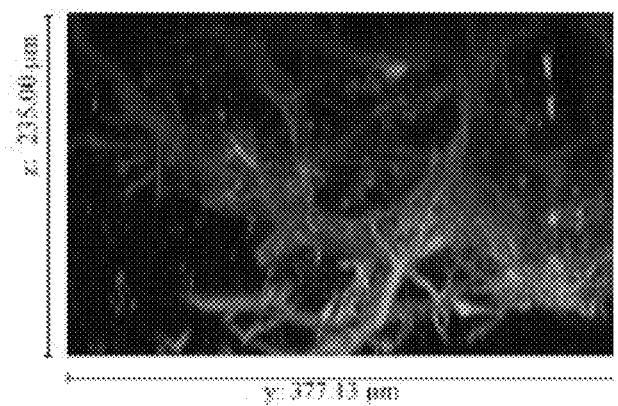
Figure 4:
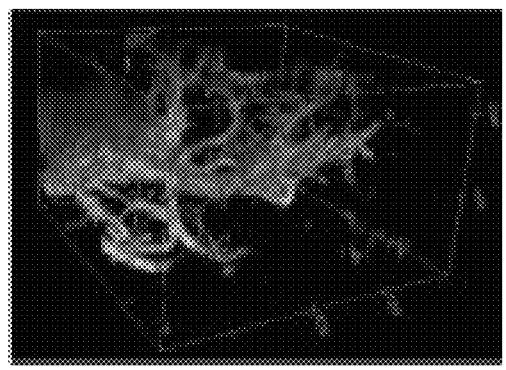
Figure 4:
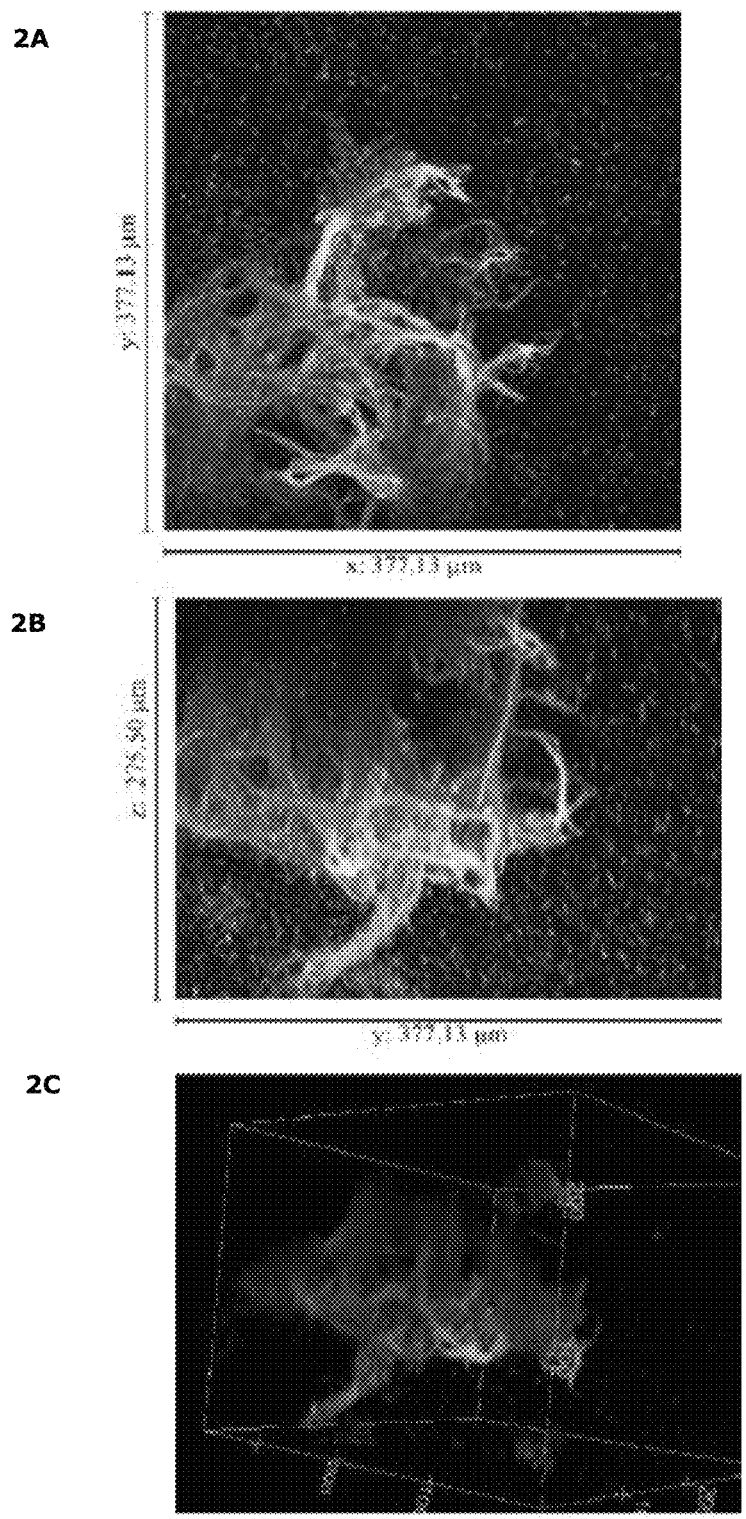
Figure 4:
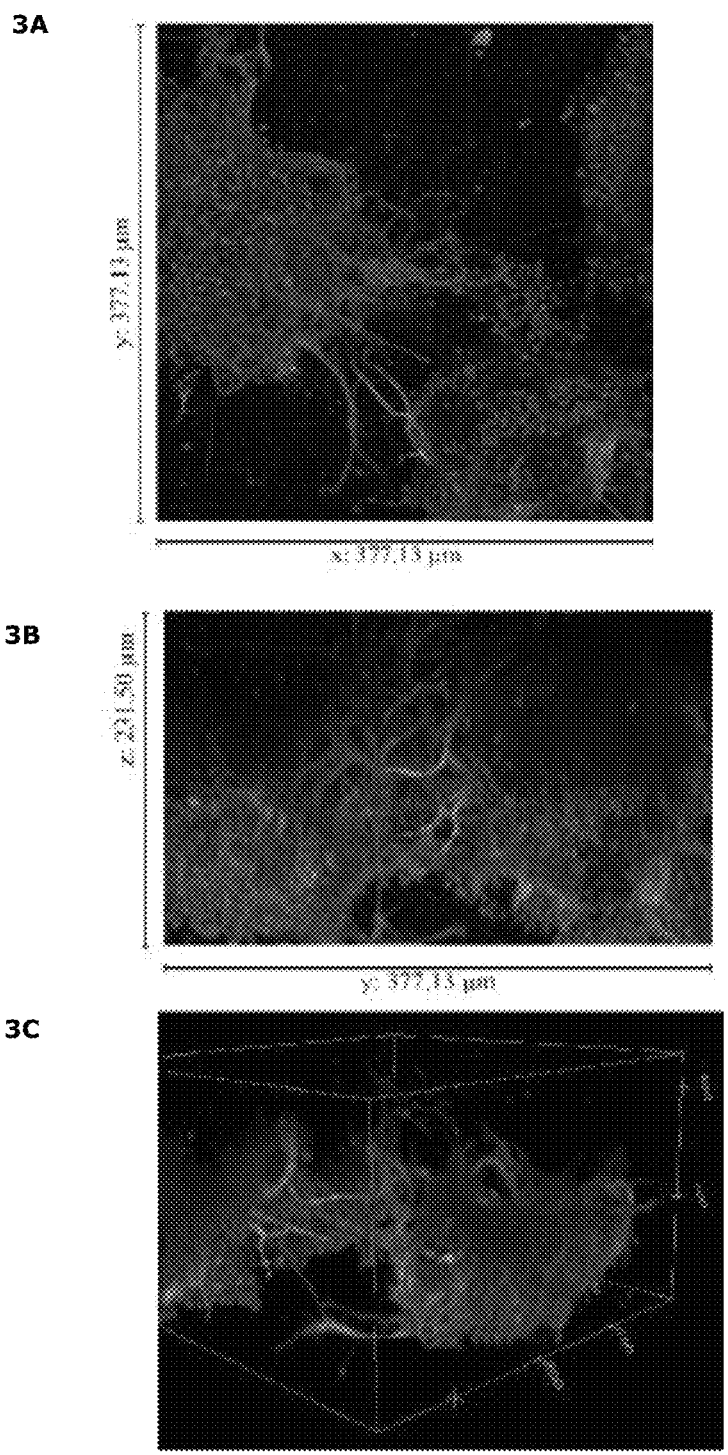

Results were quite similar between Growdex 1.50% and Growdex 1.00%. Neurite outgrowth was seen from cell aggregates (FIG. 4, stacks 1-3). Amount of neurite outgrowth varied between aggregates. In some samples incomplete antibody washout caused bright fluorescent dots (FIG. 4, stack 2).

aNFC 0.65%

Figure 5:
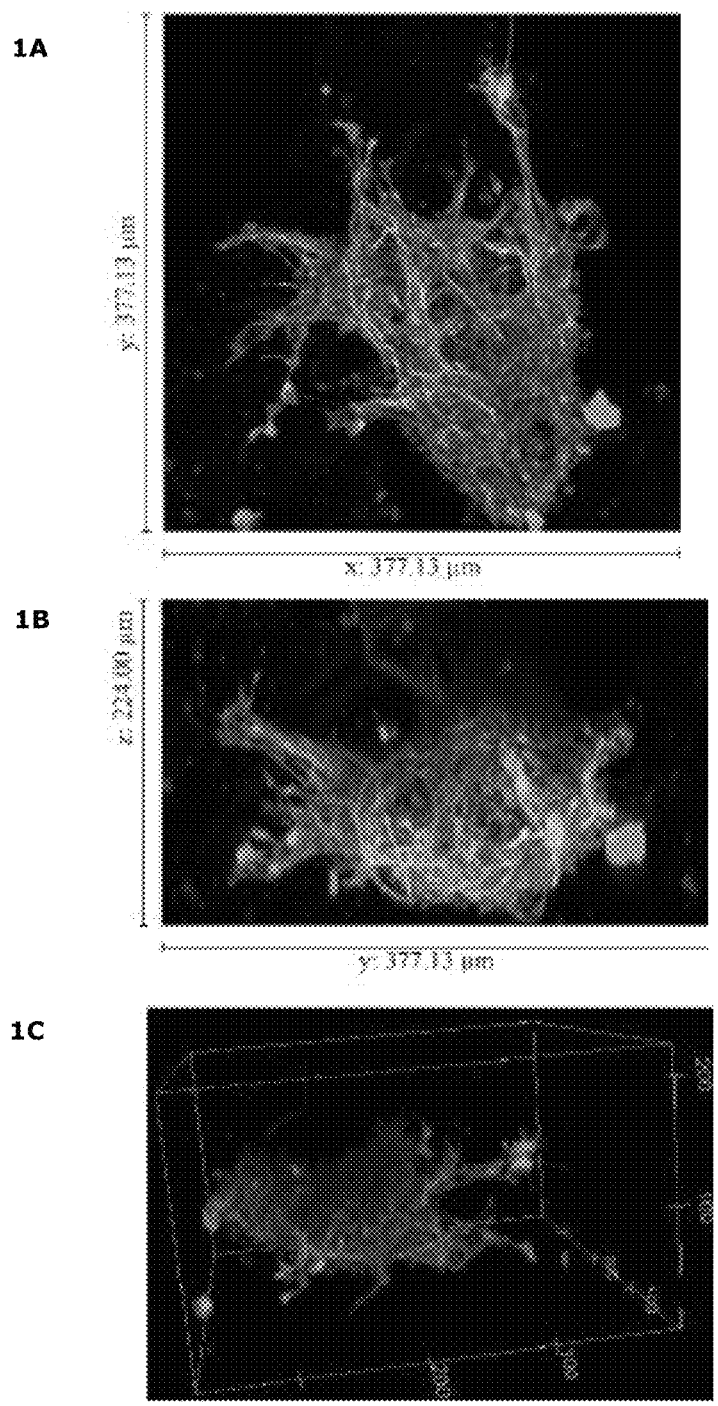
FIG. 5 shows confocal images from cell cultured as embedded within aNFC 0.65% hydrogel for two weeks. Three confocal stacks (1, 2 and 3) are presented as maximal intensity x-projection from top to bottom (A), maximal intensity projection from side and as 3D rendered visualization. In x*y plane the imaged area is 377.13 µm*377.13 µm in all images (A). The height of the confocal stack varies (z-direction, B). Both A and B images are in same scale. All presented images are from sample volume 60 µl. Markers in the images DAPI (blue), MAP-2 (green) and B-tubulin III (red)
Figure 5:
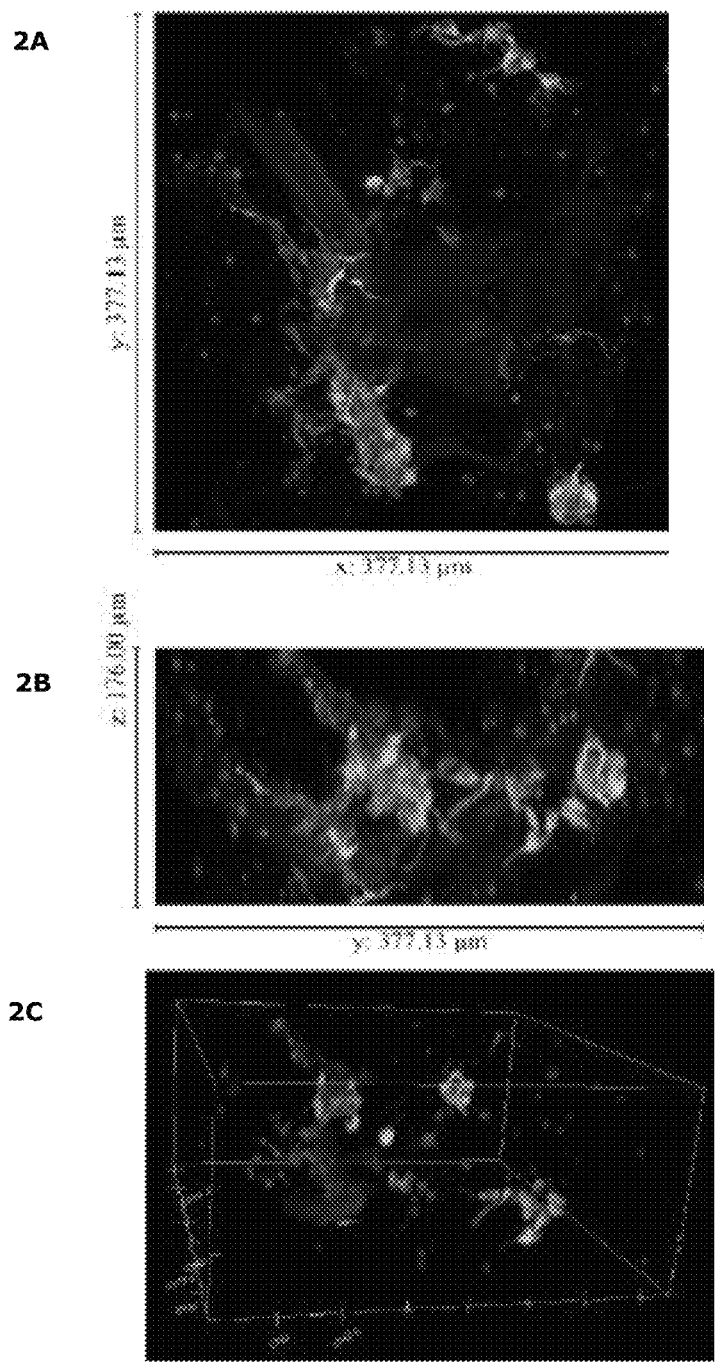
Figure 5:
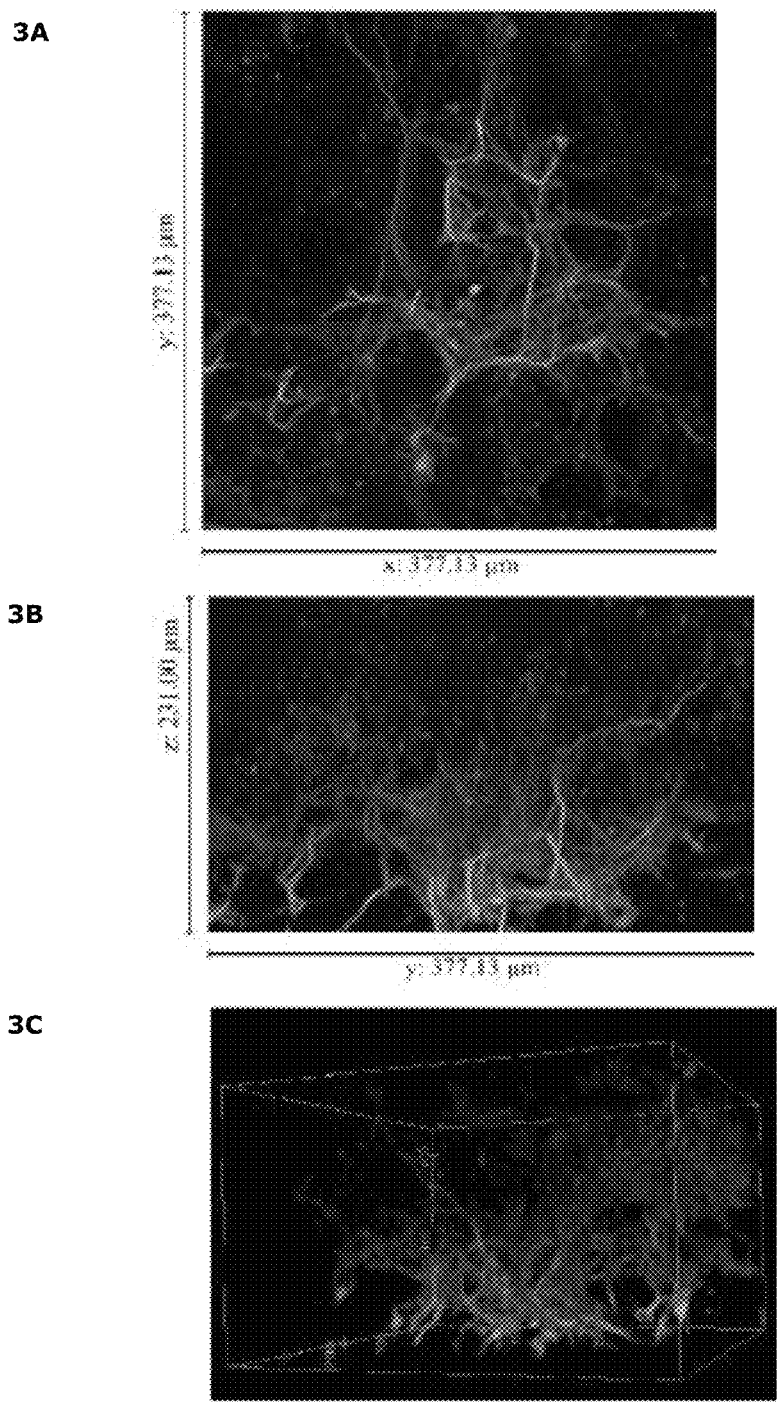

The aNFC 0.65% hydrogel supported neurite outgrowth from aggregates (FIG. 5, stacks 1 and 3) as well as neurite growth of single cells (FIG. 5, stacks 2).

aNFC 0.45%

Figure 6:
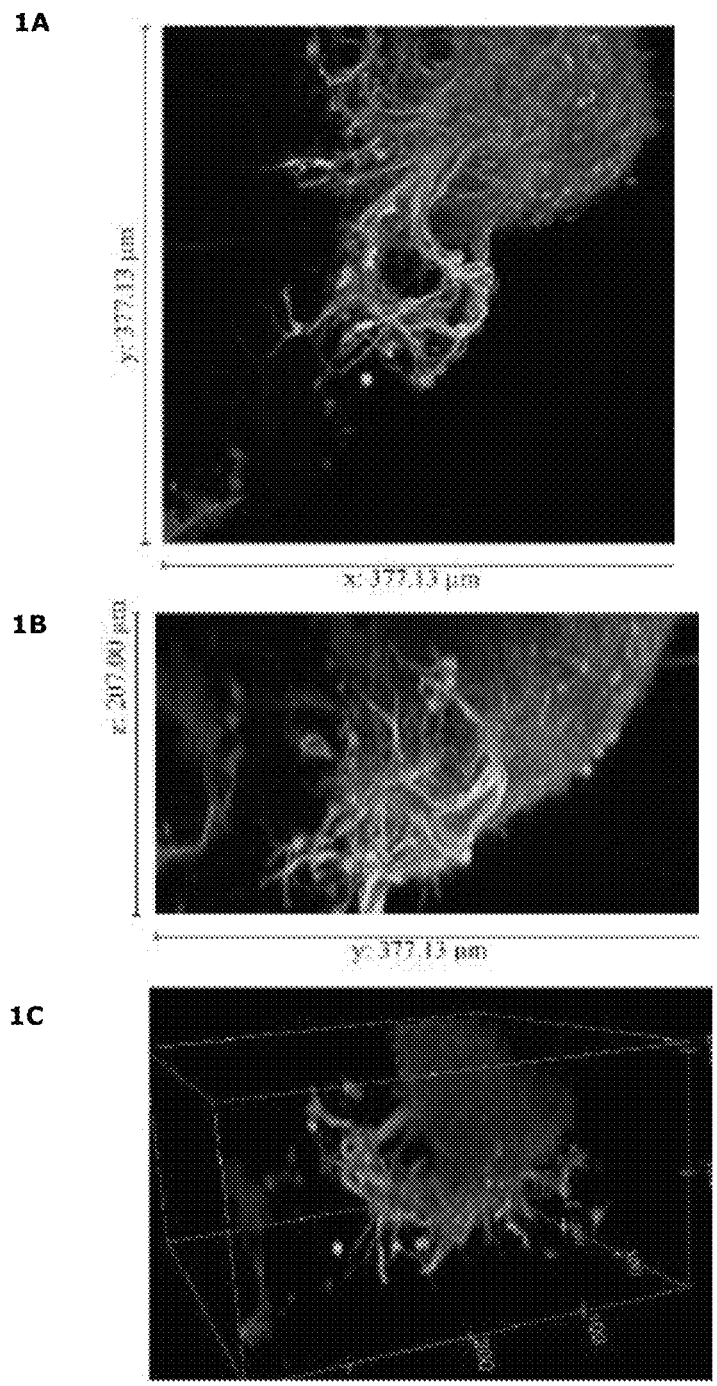
FIG. 6 shows confocal images from cell cultured as embedded within aNFC 0.45% hydrogel for two weeks. Three confocal stacks (1, 2 and 3) are presented as maximal intensity x-projection from top to bottom (A), maximal intensity projection from side and as 3D rendered visualization. In x*y plane the imaged area is 377.13 µm*377.13 µm in all images (A). The height of the confocal stack varies (z-direction, B). Both A and B images are in same scale. Images 1 and 3 are from sample volume 60 µl and image 2 is from sample volume 80 µl. Markers in the images DAPI (blue), MAP-2 (green) and B-tubulin III (red).
Figure 6:
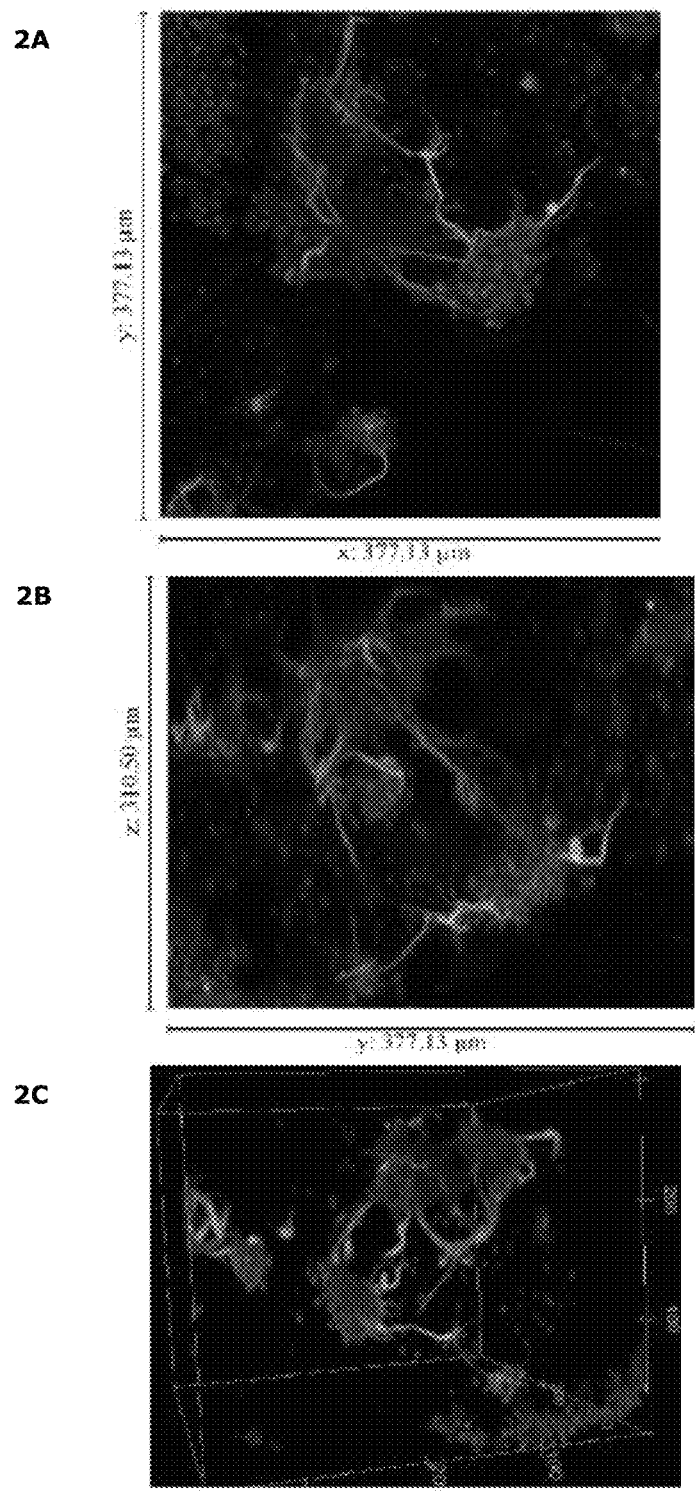
Figure 6:
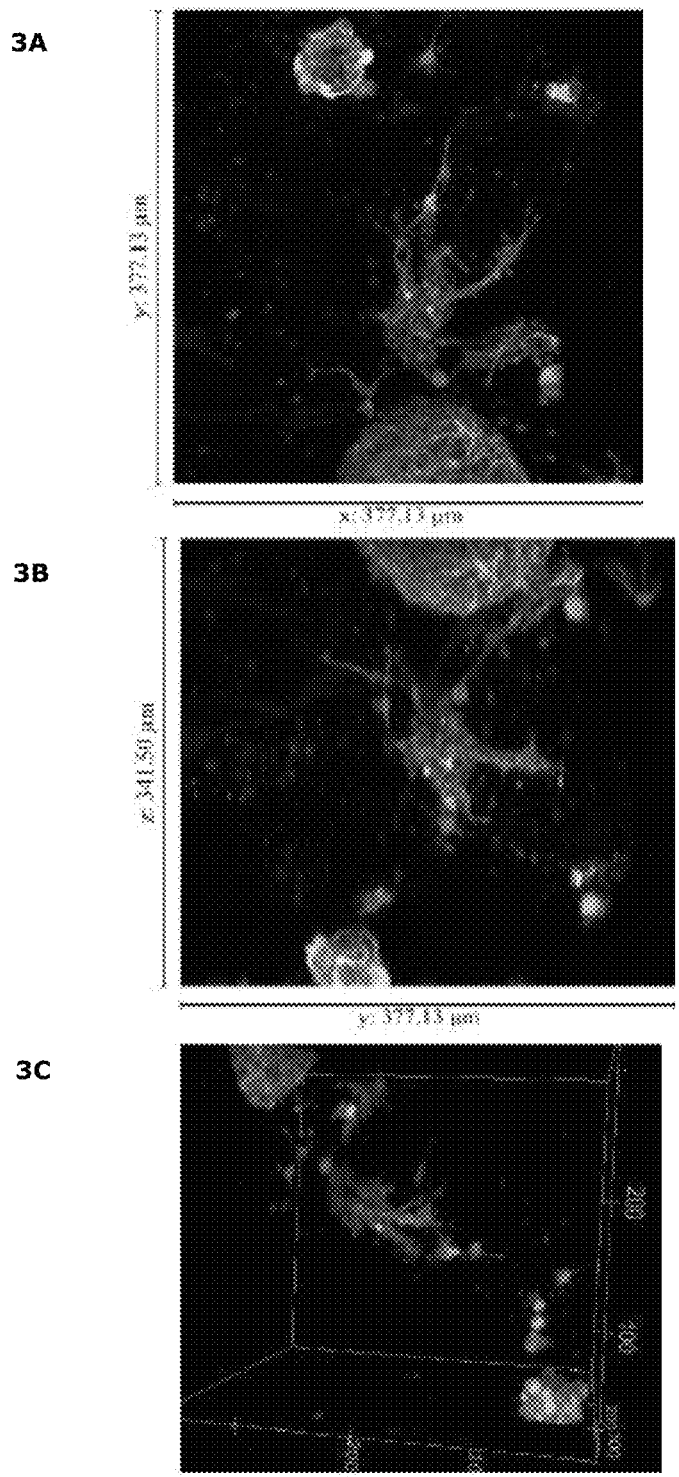

The aNFC 0.45% hydrogel supported neurite outgrowth from aggregates (FIG. 6, stacks 1 and 3) as well as neurite growth of single cells (FIG. 6, stacks 2 and 3).

aNFC 0.30%

Figure 7:
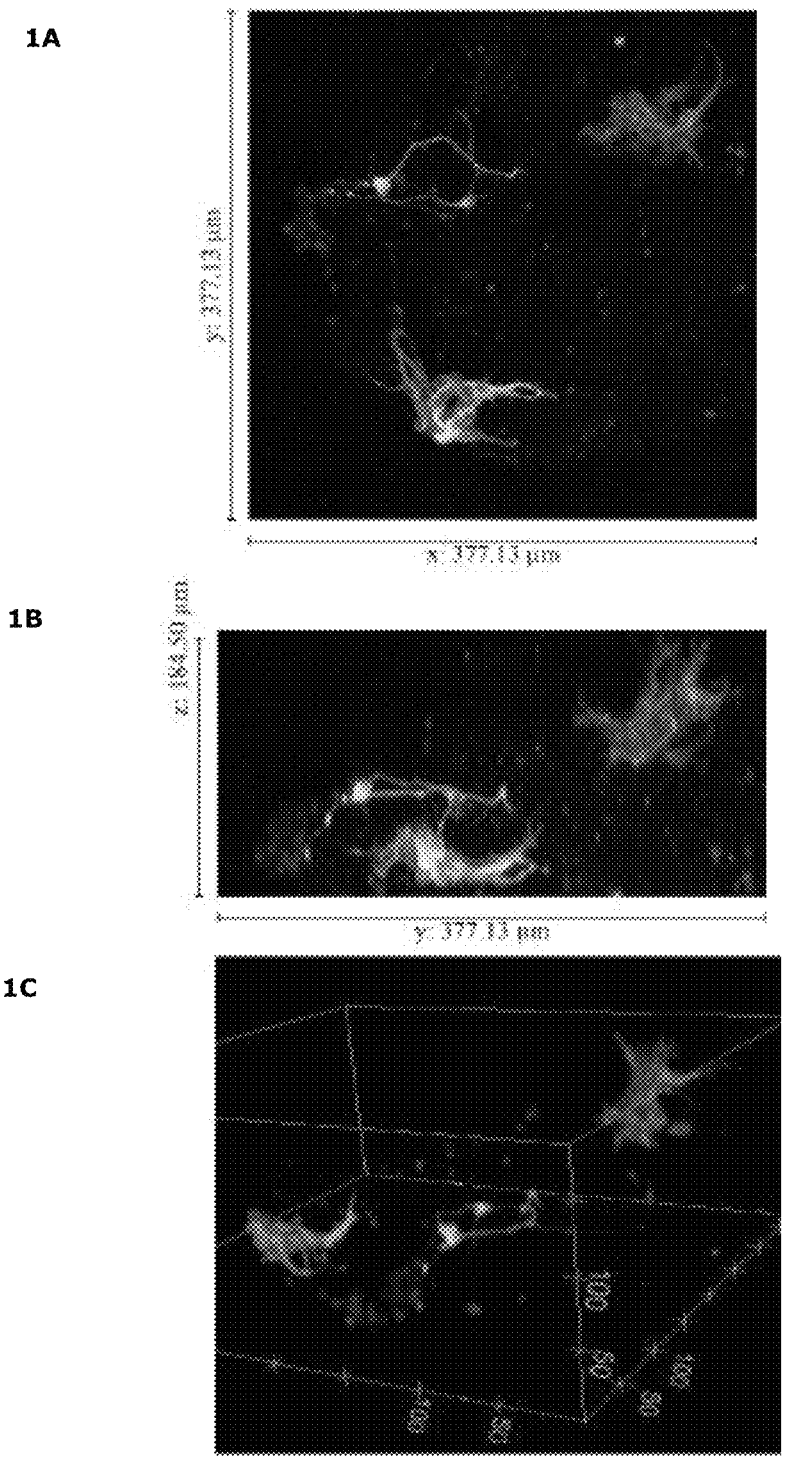
FIG. 7 shows confocal images from cell cultured as embedded within aNFC 0.30% hydrogel for two weeks. Three confocal stacks (1, 2 and 3) are presented as maximal intensity x-projection from top to bottom (A), maximal intensity projection from side and as 3D rendered visualization. In x*y plane the imaged area is 377.13 µm*377.13 µm in all images (A). The height of the confocal stack varies (z-direction, B). Both A and B images are in same scale. Image 1 is from sample volume 60 µl and images 2 and 3 are from sample volume 80 µl. Markers in the images DAPI (blue), MAP-2 (green) and B-tubulin III (red).
Figure 7:
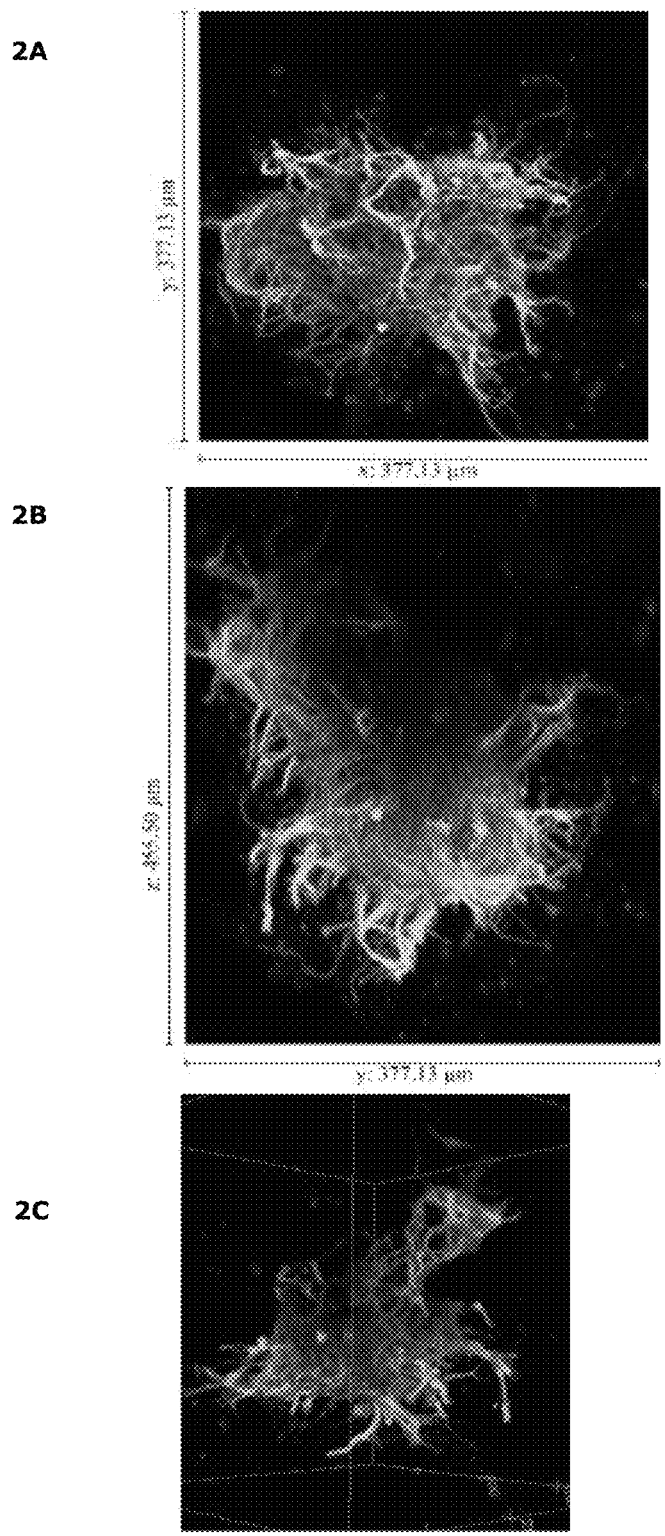
Figure 7:
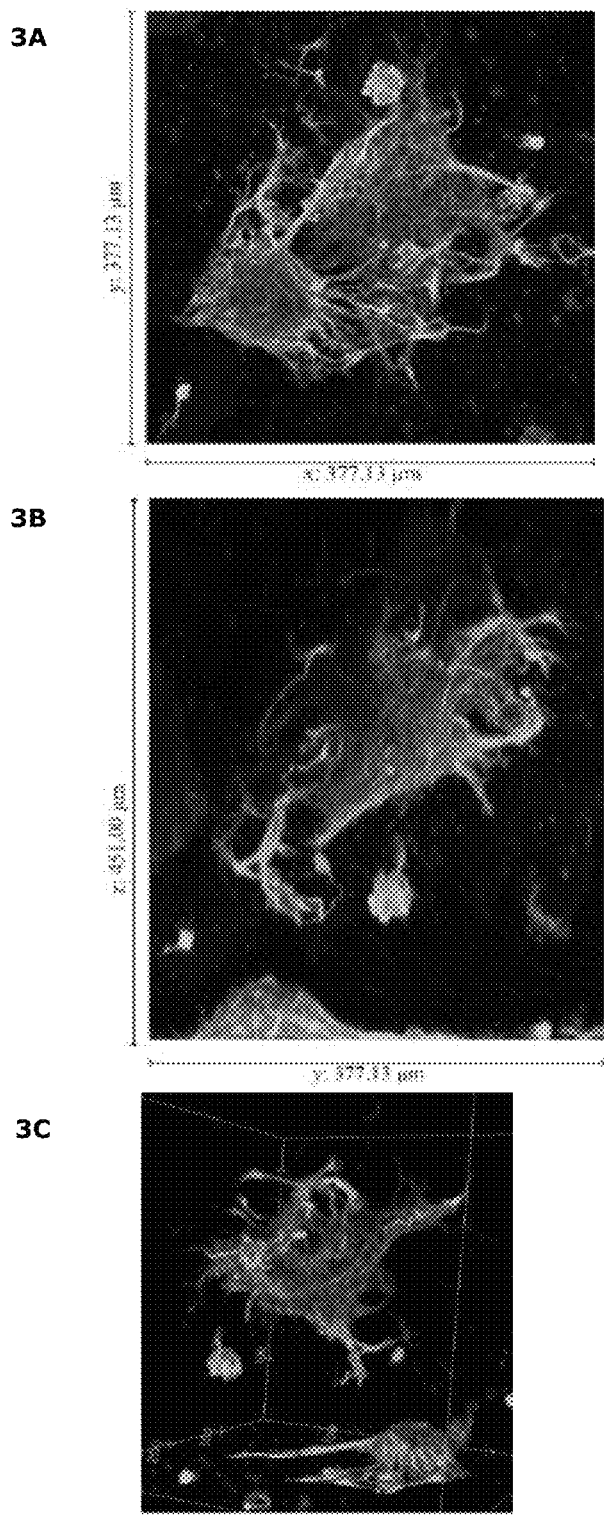

The aNFC 0.30% hydrogel was very supportive for single cells neurite growth (FIG. 7, stack 1) and supported massive neurite outgrowth from cell aggregates (FIG. 7, stacks 2 and 3).

According to these results it can concluded:
1. The aNFC hydrogels were better for supporting single cells neurite outgrowth
2. Substantial neurite outgrowth was detected also from cell aggregates in both Growdex and aNFC hydrogels.
3. Hydrogel volume (80 µl or 60 µl) had no effect on the quality of imaging.

The handling of both hydrogels was successful and it was possible to produce homogenous cell suspension inside the hydrogel matrix. The aNFC hydrogels were much easier to prepare. Some amount of gel loss occurred during immunocytochemical staining but none of the samples were completely lost in this experiment. This effect was prominent with smaller sample volumes (60 µl).

Figure 2:
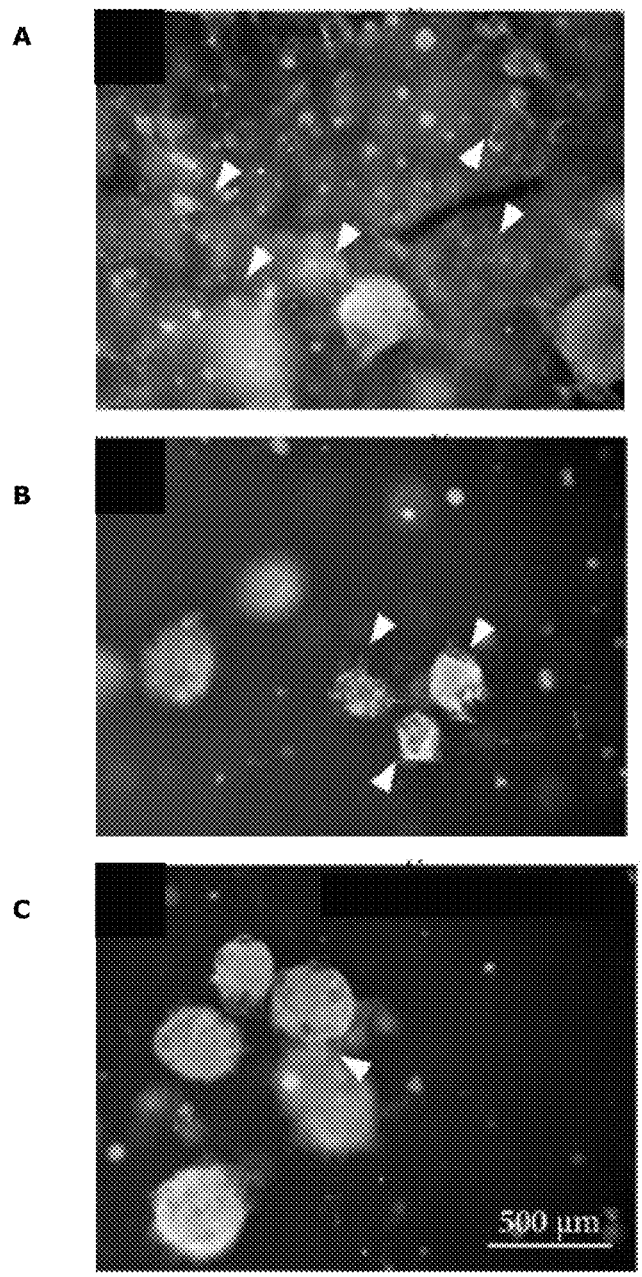
FIG. 2 shows examples of hydrogel samples with good growth (A), moderate growth (B) and poor growth (c). Arrow heads show neurite outgrowth in the images. Markers in the images DAPI (blue), MAP-2 (green) and B-tubulin III (red). Scale bar in images is 500 µm. Hydrogels in the images are aNFC 0.30% 60 µl (A), aNFC 0.65% 60 µl (B), and Growdex 1.50% 60 µl (C).

Both Growdex and aNFC hydrogels contained substantial amounts of live neurons after 2 weeks of culturing. Both hydrogels contained neuronal cell aggregates with robust neurite outgrowth. In best cases, the formed networks filled up the whole hydrogel block (FIG. 2, A).

Figure 8:
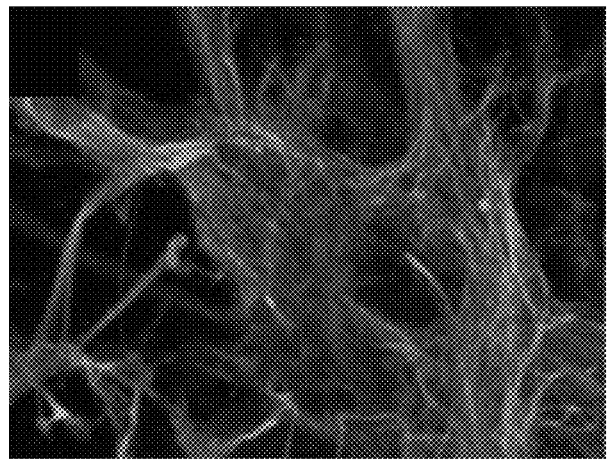
FIG. 8 shows close up images from neurite outgrowth from cell aggregates (FIG. 4 1A) vs from single cells (FIG. 7 1A) presented as maximal intensity x-projection from top to bottom. Markers in the images DAPI (blue), MAP-2 (green) and B-tubulin III (red).
Figure 8:
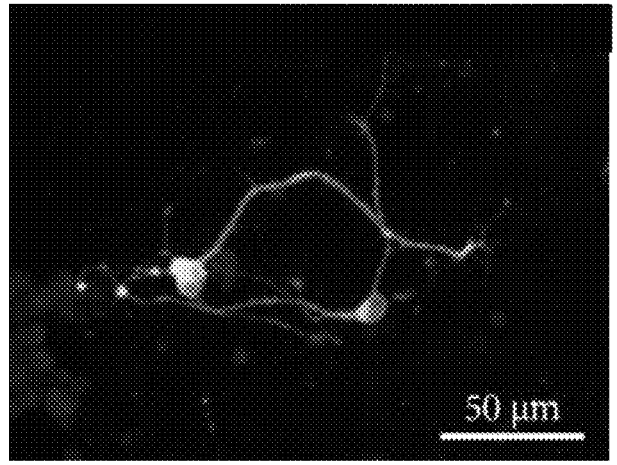

The main difference observed between the two studied hydrogels was in growth of single cells and their neurite outgrowth. The Growdex hydrogels were mainly supporting neurite outgrowth only from cell aggregates (FIG. 8 A) whereas the aNFC hydrogels also supported neurite growth of single cells (FIG. 8 B). For single neurons, it takes more time to form 3D networks. Thus, it can be hypothesized that prolonged culturing time would have been beneficial to observe stronger network formation in these cases.

Depending on application, both types of neurite outgrowth can be seen beneficial. To our experience, these gels showed to be very good in supporting neurite outgrowth, one of the most important feature in neuronal 3D cell culturing.

Expanding cells grow better in aNFC compared to native grade which is currently used. Cells like to orient towards charged fibrils. Lower solid contents in anionic hydrogel enable more free movement of cells. Anionic hydrogels could be beneficially used in applications were functional cell networks are required.

Measurement of Turbidity

A nanofibrillar cellulose sample was diluted in water to a concentration below the gel point of said nanofibrillar cellulose, and turbidity of the diluted sample was measured. The turbidity of the nanofibrillar cellulose samples was measured at the concentration of 0.1%. HACH P2100 Turbidometer with a 50 ml measuring vessel was used for turbidity measurements. The dry matter of the nanofibrillar cellulose sample was determined and 0.5 g of the sample, calculated as dry matter, was loaded in the measuring vessel, which was filled with tap water to 500 g and vigorously mixed by shaking for about 30 s. Without delay the aqueous mixture was divided into 5 measuring vessels, which were inserted in the turbidometer. Three measurements on each vessel were carried out. The mean value and standard deviation were calculated from the obtained results, and the final result was given as NTU units. The novel nanofibrillar cellulose product had a typical turbidity below 200, preferably below 150 NTU in the above mentioned measurement conditions.

Rheological Measurements

To verify the success of fibrillation, rheological measurements of the samples in the form of nanofibrillar cellulose hydrogels were carried out with a stress controlled rotational rheometer (ARG2, TA instruments, UK) equipped with four-bladed vane geometry. Samples were diluted with deionized water (200 g) to a concentration of 0.5 w % and mixed with Hand mixer. Rheometer measurement was carried out for the sample. The diameters of the cylindrical sample cup and the vane were 30 mm and 28 mm, respectively, and the length was 42 m. The stress sweep was measured in a shear stress range of 0.001-100 Pa at the frequency 0.1 Hz, at 25° C.

Figure 9:
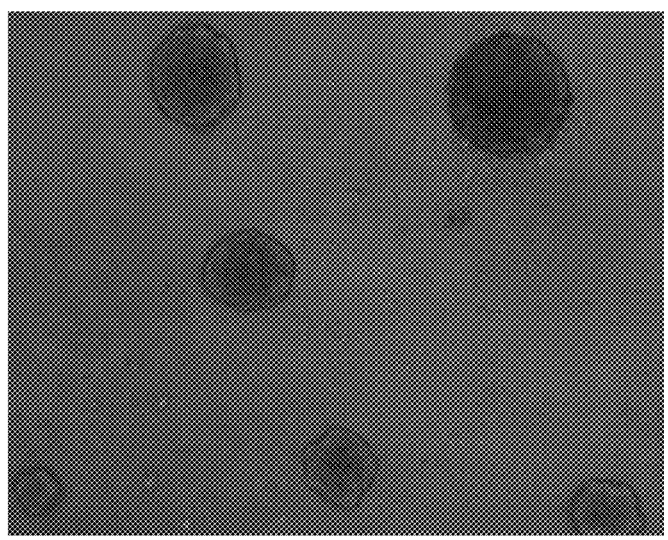
FIG. 9 shows round human dermal fibroblasts (HDF) spheroid formation in GrowDex hydrogel (FIG. 9A). In GrowDexT hydrogel HDF cells grow in clusters and form protrusions, suggesting that the cells sense the environment (FIG. 9B).
Figure 9:
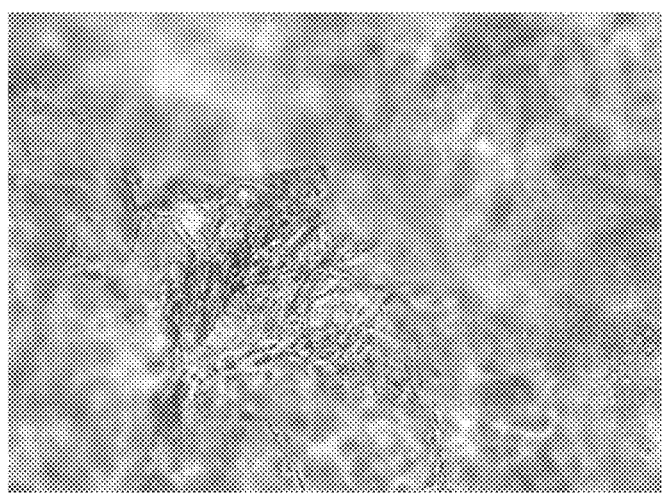

Example 2. Testing Nanofibrillar Cellulose Based Hydrogels with Human Dermal Fibroblast Cells Human dermal fibroblasts (HDF) were mixed with NFC hydrogel GrowDex or anionic NFC hydrogel GrowDexT. Cell-hydrogels were transferred to 96-well plate, 60 µl cell-hydrogel per well, and 100 µl cell culture medium (DMEM supplemented with serum) was added on top of the hydrogels. Cells were cultured in 37° C. at 5% $CO_2$ for 7 days and the growth properties (proliferation, morphology, migration) were analysed by brightfield live cell imaging with automated Cell-IQ microscope (Chip-Man Technologies). Results show round HDF spheroid formation in GrowDex (FIG. 9 A). In GrowDexT HDF cells grow in clusters and form protrusions, suggesting that the cells sense the environment (FIG. 9 B).

REFERENCES

Ahola, S., Turon, X., Osterberg, M., Laine, J., Rojas, O. J. 2008. Enzymatic hydrolysis of native cellulose nanofibrils and other cellulose model films: effect of surface structure. Langmuir, 24, 11592-11599.

Hoffman, A. S., 2002. Hydrogels for biomedical applications. Advanced Drug Delivery Reviews, vol. 54, no. 1, pp. 3-12.

Geckil, H., Xu, F., Zhang, X., Moon, S. and Demirci, U. 2010. Engineering hydrogels as extracellular matrix mimics. Nanomedicine (Lond). 5(3): p. 469-84.

Koivisto, J. T., Joki, T., Parraga, J., Rääkkönen, R., Ylä-Outinen, L., Salonen, L., Jonkkari, I., et al. 2017. Bioamine-Crosslinked Gellan Gum Hydrogel for Neural Tissue Engineering. Biomedical Materials, February, 1-38. doi:10.1088/1748-605X/aa62b0.

Kuthcarlapati et al., 2008. Metals Materials and Processes 20(3):307-314.

Lappalainen, R. S., Salomäki, M., Ylä-Outinen, L., Heikkllä, T. J., Hyttinen J. K., Pihlajamäki, K., Suuronen, R., Skottman, H., and Narkilahti, S. 2010. Similarly Derived and Cultured hESC Lines Show Variation in Their Developmental Potential towards Neuronal Cells in Long-Term Culture. Regenerative Medicine 5 (5): 749-62. doi: 10.2217/rme.10.58.

Nisbet D R, Crompton K E, Horne M K et al., 2008. Neural tissue engineering of the CNS using hydrogels. J Biomed Mater Res B Appl Biomater 87: 251-263.

Ylä-Outinen, L., Joki, T., Varjola, M., Skottman, H., and Narkilahti, S., 2014. Three-Dimensional Growth Matrix for Human Embryonic Stem Cell-Derived Neuronal Cells. Journal of Tissue Engineering and Regenerative Medicine 8 (3): 186-94. doi:10.1002/term.1512.

The invention claimed is:

1. A composition configured for culture of expanding neuronal cells, said composition comprising:
   0.05-0.35 wt % of mechanically disintegrated plant-derived anionic nanofibrillar cellulose having a degree of substitution of between 0.08 and 0.3 and a storage modulus between 5 and 20 Pa when dispersed to a concentration of 0.5 wt % in water, the nanofibrillar cellulose being in a form of hydrogel,
   wherein said plant-derived anionic nanofibrillar cellulose comprises TEMPO oxidized nanofibrillar cellulose, and
   wherein said plant-derived anionic nanofibrillar cellulose has a loss tangent greater than 1 when the range of storage modulus is between 1-20 Pa when dispersed to a concentration of 0.5 w % in water.

2. The composition according to claim 1, wherein the cells grow protrusions or projections.

3. The composition according to claim 1, wherein said plant-derived anionic nanofibrillar cellulose comprises nanofibrillar cellulose manufactured from TEMPO oxidized cellulosic raw material having a carboxylate content above 0.5 mmol/g based on the weight of the cellulosic raw material.

4. The composition according to claim 1, wherein said plant-derived anionic nanofibrillar cellulose includes cellulose I.

5. The composition according to claim 1, wherein said plant-derived anionic nanofibrillar cellulose comprises carboxymethylated nanofibrillar cellulose, sulphonated nanofibrillar cellulose, or the combination thereof.

6. The composition according to claim 1, wherein said plant-derived anionic nanofibrillar cellulose has a loss tangent less than 0.3 when a shear stress is less than 0.5 Pa.

7. The composition according to claim 1, wherein said plant-derived anionic nanofibrillar cellulose has a carboxylate content above 0.75 mmol/g based on the weight of the cellulosic raw material.

8. The composition according to claim 1, wherein said plant-derived anionic nanofibrillar cellulose has a turbidity of 20 NTU or less in water at concentration of 0.1 w %.

9. The composition according to claim 1, wherein said composition is transparent.

10. The composition according to claim 1, further comprising one or more additives selected from extra cellular matrix components, serum, growth factors, proteins, or any combination thereof.

11. The composition according to claim 1, wherein the composition is in the form of a matrix, the composition further comprising living neuronal cells present in said matrix in a three-dimensional or two-dimensional arrangement.

12. A method for manufacturing a composition configured for culture of expanding neuronal cells, said method comprising:
   a. providing plant-derived anionic nanofibrillar cellulose; and
   b. mixing said anionic nanofibrillar cellulose with water to form 0.05-0.35 wt % of mechanically disintegrated plant-derived anionic nanofibrillar cellulose having a degree of substitution of between 0.08 and 0.3 and a storage modulus between 5 and 20 Pa when dispersed to a concentration of 0.5 wt % in water, the anionic nanofibrillar cellulose being in a form of hydrogel, wherein said plant-derived anionic nanofibrillar cellulose comprises TEMPO oxidized nanofibrillar cellulose, and wherein said plant-derived anionic nanofibrillar cellulose has a loss tangent greater than 1 when the range of storage modulus is between 1-20 Pa when dispersed to a concentration of 0.5 w % in water.

13. A method for three-dimensional or two-dimensional culturing of cells or tissues, the method comprising:
   providing a composition for culture of expanding cells, the composition comprising 0.05-0.35 wt % of mechanically disintegrated plant-derived anionic nanofibrillar cellulose having a degree of substitution of between 0.08 and 0.3 and a storage modulus between 5 and 20 Pa when dispersed to a concentration of 0.5 wt % in water, the anionic nanofibrillar cellulose being in a form of hydrogel, wherein said plant-derived anionic nanofibrillar cellulose comprises TEMPO oxidized nanofibrillar cellulose, and wherein said plant-derived anionic nanofibrillar cellulose has a loss tangent greater than 1 when the range of storage modulus is between 1-20 Pa when dispersed to a concentration of 0.5 w % in water;
   inoculating at least one neuronal cell within the composition; and
   culturing to obtain a cell mass.

14. The method according to claim 13, wherein the culturing includes culturing at least two neuronal cell types of different origin as a co-culture.

15. The method according to claim 13, further comprising enzymatically treating the composition with a cellulase for a time sufficient to at least partly release cell mass.

16. The method according to claim 15, further comprising inactivating or removing the cellulase from the cell mass after enzymatic treatment.

* * * * *